(12) United States Patent
Bhatt et al.

(10) Patent No.: US 12,182,245 B2
(45) Date of Patent: Dec. 31, 2024

(54) SYSTEMS AND METHODS FOR VIRTUAL ASSISTANT ENHANCED ACCESS OF SERVICES RELATED TO PRIVATE INFORMATION USING A VOICE-ENABLED DEVICE

(71) Applicant: ELEVANCE HEALTH, INC., Indianapolis, IN (US)

(72) Inventors: Anil Bhatt, Indianapolis, IN (US); Widya Harianto, Woodland Hills, CA (US); Elizabeth Basnight, Indianapolis, IN (US); Narasimha Adapa, Moorpark, CA (US); Kennis Dees, Palm Harbor, FL (US); Trupti Doshi, Mason, OH (US); Elizabeth Kwo, Cambridge, MA (US); Anthony Nguyen, Pacific Palisades, CA (US); Alicia Staffier, Worcester, MA (US); Kiran Kumar Simhadri, San Jose, CA (US)

(73) Assignee: Elevance Health, Inc., Indianapolis, IN (US)

( * ) Notice: Subject to any disclaimer, the term of this patent is extended or adjusted under 35 U.S.C. 154(b) by 0 days.

(21) Appl. No.: 18/550,873

(22) PCT Filed: Mar. 16, 2022

(86) PCT No.: PCT/US2022/020579
§ 371 (c)(1),
(2) Date: Sep. 15, 2023

(87) PCT Pub. No.: WO2022/197820
PCT Pub. Date: Sep. 22, 2022

(65) Prior Publication Data
US 2024/0037205 A1     Feb. 1, 2024

Related U.S. Application Data

(60) Provisional application No. 63/209,610, filed on Jun. 11, 2021, provisional application No. 63/161,798, filed on Mar. 16, 2021.

(51) Int. Cl.
*G10L 17/22* (2013.01)
*G06F 3/16* (2006.01)
(Continued)

(52) U.S. Cl.
CPC .............. *G06F 21/32* (2013.01); *G06F 3/167* (2013.01); *G06F 16/638* (2019.01); *G10L 17/02* (2013.01);
(Continued)

(58) Field of Classification Search
CPC . G10L 15/22; G10L 2015/223; G10L 15/265; G10L 5/30; G10L 2105/088;
(Continued)

(56) References Cited

U.S. PATENT DOCUMENTS

| 11,955,125 B2 * | 4/2024 | Ho ........................... G06F 3/167 |
| 2005/0188220 A1 * | 8/2005 | Nilsson ................... H04L 67/04 726/5 |

(Continued)

OTHER PUBLICATIONS

International Search Report and Written Opinion dated Jun. 8, 2022 for International Patent Application No. PCT/US202/020579, 10 pages.

*Primary Examiner* — Olujimi A Adesanya
(74) *Attorney, Agent, or Firm* — Morgan, Lewis & Bockius LLP

(57) ABSTRACT

A system and method for interacting with a voice-assisted member interface hosted by a provider backend server of a provider using a voice enabled-apparatus hosted by an apparatus vendor separate and distinct from the provider, the voice-enabled apparatus including a microphone unit, a speaker and a processor coupled to the microphone unit and the speaker, the processor configured to cause the voice-enabled apparatus to perform one or more functions in response to audio signals received at the microphone unit.

13 Claims, 23 Drawing Sheets

(51) Int. Cl.
- *G06F 16/638* (2019.01)
- *G06F 21/32* (2013.01)
- *G10L 15/22* (2006.01)
- *G10L 17/02* (2013.01)
- *G10L 17/04* (2013.01)
- *G10L 17/14* (2013.01)
- *G10L 17/24* (2013.01)
- *G16H 10/60* (2018.01)

(52) U.S. Cl.
CPC .............. *G10L 17/04* (2013.01); *G10L 17/14* (2013.01); *G10L 17/24* (2013.01); *G16H 10/60* (2018.01)

(58) Field of Classification Search
CPC ......... G10L 15/18; G10L 17/22; G10L 15/26; G06F 3/167; G06F 16/3329
See application file for complete search history.

(56) References Cited

U.S. PATENT DOCUMENTS

| | | | |
|---|---|---|---|
| 2012/0278093 A1* | 11/2012 | Amundson | G16H 10/20 705/2 |
| 2018/0096690 A1* | 4/2018 | Mixter | G10L 21/0216 |
| 2018/0366125 A1* | 12/2018 | Liu | G10L 17/06 |
| 2019/0122001 A1* | 4/2019 | Bradley | H04W 12/02 |
| 2019/0272831 A1* | 9/2019 | Kajarekar | G10L 17/06 |
| 2020/0152176 A1* | 5/2020 | Eraslan | G10L 15/08 |
| 2020/0243174 A1* | 7/2020 | Burgess | G06V 30/40 |
| 2020/0350072 A1* | 11/2020 | McEwing | G16H 50/70 |
| 2020/0380981 A1 | 12/2020 | Tom | |
| 2020/0389314 A1 | 12/2020 | Kunnath et al. | |
| 2021/0042786 A1 | 2/2021 | Tiruveedhula | |
| 2021/0326421 A1* | 10/2021 | Khoury | G10L 17/08 |
| 2022/0245270 A1* | 8/2022 | De Araujo | G16H 40/67 |
| 2023/0359765 A1* | 11/2023 | Selvaraju | G06F 21/6245 |

* cited by examiner

SYSTEMS AND METHODS FOR VIRTUAL ASSISTANT ENHANCED ACCESS OF SERVICES RELATED TO PRIVATE INFORMATION USING A VOICE-ENABLED DEVICE

CROSS-REFERENCE TO RELATED APPLICATIONS

This application is a national stage entry of International Application No. PCT/US2022/020579 filed Mar. 16, 2022, which claims the benefit of U.S. Provisional Patent Application No. 63/161,798 filed Mar. 16, 2021 entitled "Systems and Methods for Virtual Assistant Enhanced Access of Services Related to Private Information Using a Voice-Enabled Device", and U.S. Provisional Patent Application No. 63/209,610 filed Jun. 11, 2021 entitled "Systems and Methods for Virtual Assistant Enhanced Access of Services Related to Private Information Using a Voice-Enabled Device", each of which is incorporated by reference herein in its entirety.

BACKGROUND OF THE INVENTION

The present invention generally relates to the field of vendors hosting services related to protected information of users and, more particularly, to integrating a user-facing voice enabled virtual assistant with protected private and personal information to provide customers with on-demand secure access to services their protected information.

BRIEF SUMMARY OF THE INVENTION

In one embodiment there is a method for interacting with a voice-assisted member interface hosted by a first provider backend server of a first provider using a voice-enabled apparatus hosted by an apparatus vendor separate and distinct from the first provider, the voice-enabled apparatus including a microphone unit, a speaker and a processor coupled to the microphone unit and the speaker, the processor configured to cause the voice-enabled apparatus to perform one or more functions in response to audio signals received at the microphone unit. The method includes receiving an audio input signal from a user at the microphone unit of the voice-enabled apparatus, converting, at the voice-enabled apparatus, the audio input signal to a computer readable text format. The method further includes transmitting, from the voice-enabled apparatus to the first provider backend server, the converted audio input signal, and determining, by the first provider backend server, whether the converted audio input signal includes a request for a service provider search and one or more search criteria. The method further includes in response to the converted audio input signal including a request for a service provider search and one or more search criteria, determining whether a second provider backend server of a second provider includes an associated application programming interface, wherein the second provider is separate and distinct from the first provider. The method further includes in response to determining that the second provider backend server does include an associated application programming interface, transmitting the one or more search criteria to the associated application programming interface of the second provider backend server. The method further includes, executing, by the second provider backend server, a database search in a database in communication with the second provider backend server, based on the one or more search criteria, the database storing a plurality of records corresponding to individual service providers associated with the second provider. The method further includes, generating, by the second provider backend server, a list of search results including a subset of records, of the plurality of records stored on the database, the subset of records matching the one or more search criteria. The method further includes, transmitting, from the second provider backend server, to the first provider backend server, the list of search results, generating, from the first provider backend server a response based on the list of search results and transmitting the response to the voice-enabled apparatus, and outputting, at the speaker, an audio output signal associated with the response.

In some embodiments, the method further includes in response to determining that the second provider backend server does not include an associated application programming interface, and transmitting, from the first provider backend server, to the second provider backend server, a request for the plurality of records corresponding to individual service providers. The method may further include in response to receiving the request for the plurality of records, transmitting, from the second provider backend server to the first provider backend server, the plurality of records, and executing, by the first provider backend server, a search of the plurality of records, based on the one or more search criteria. In some embodiments, the method further includes generating, by the first provider backend server, the list of search results including the subset of records, of the plurality of records received from the second provider backend server, the subset of records matching the one or more search criteria, generating, from the first provider backend server a response based on the list of search results and transmitting the response to the voice-enabled apparatus, and outputting, at the speaker, an audio output signal associated with the response.

In some embodiments, the first provider is a healthcare insurance provider and the second provider is a healthcare provider. In some embodiments, the second provider backend server is a plurality of second provider backend servers each associated with a provider separate and distinct from the first provider. In some embodiments, the output audio signal includes a prompt to the user to perform a subsequent user action. In some embodiments, the voice-enabled apparatus is HIPAA compliant. In some embodiments, the one or more search criteria includes one or more of gender, age, primary healthcare specialty, and languages spoken.

In another embodiment, there is a system for interacting with a voice-assisted member interface hosted by a first provider backend server of a first provider including a voice-enabled apparatus including a microphone unit, a speaker and a processor coupled to the microphone unit and the speaker, the processor configured to cause the voice-enabled apparatus to perform one or more functions in response to audio signals received at the microphone unit. The processer is configured to receive an audio input signal from a user at the microphone unit of the voice-enabled apparatus, convert the audio input signal to a computer readable text format, and transmit, from the voice-enabled apparatus to the first provider backend server, the converted audio input signal. The system further includes a first provider backend server configured to determine whether the converted audio input signal includes a request for a service provider search and one or more search criteria, in response to the converted audio input signal including a request for a service provider search and one or more search criteria, determining whether a second provider backend server of a second provider includes an associated application programming interface, wherein the second provider is separate and distinct from the first provider, and in response to determining that the second provider backend server does include an associated application programming interface, transmitting the one or more search criteria to the associated application programming interface of the second provider backend server. The system further includes, a second provider backend server configured to execute a database search in a database in communication with the second provider backend server, based on the one or more search criteria, the database storing a plurality of records corresponding to individual service providers associated with the second provider, generate a list of search results including a subset of records, of the plurality of records stored on the database, the subset of records matching the one or more search criteria, and transmit, from the second provider backend server, to the first provider backend server, the list of search results. The first provider backend server is further configured to generate a response based on the list of search results and transmitting the response to the voice-enabled apparatus, and the voice-enabled apparatus is further configured to output at the speaker, an audio output signal associated with the response.

In some embodiments, the first provider backend server is further configured to in response to determining that the second provider backend server does not include an associated application programming interface, transmit to the second provider backend server, a request for the plurality of records corresponding to individual service providers. The second backend server may further be configured to in response to receiving the request for the plurality of records, transmitting, from the second provider backend server to the first provider backend server, the plurality of records. The first provider backend server may be further configured to execute a search of the plurality of records, based on the one or more search criteria, generate the list of search results including the subset of records, of the plurality of records received from the second provider backend server, the subset of records matching the one or more search criteria, and generate a response based on the list of search results and transmit the response to the voice-enabled apparatus.

In some embodiments, the first provider is a healthcare insurance provider and the second provider is a healthcare provider. In some embodiments, the second provider backend server is a plurality of second provider backend servers each associated with a provider separate and distinct from the first provider. In some embodiments, the output audio signal includes a prompt to the user to perform a subsequent user action. In some embodiments, the voice-enabled apparatus is HIPAA compliant.

In another embodiment there is a method for interacting with a voice-assisted member interface hosted by a provider backend server of a provider using a voice enabled-apparatus hosted by an apparatus vendor separate and distinct from the provider, the voice-enabled apparatus including a microphone unit, a speaker and a processor coupled to the microphone unit and the speaker, the processor configured to cause the voice-enabled apparatus to perform one or more functions in response to audio signals received at the microphone unit. The method includes receiving, at a user interface associated with the voice-enabled apparatus, first authentication credentials associated with the vendor of the voice-enabled apparatus, and transmitting, by the processor of the voice-enabled apparatus to a vendor backend server of the voice-enabled apparatus, a first request to authenticate the user at the voice-enabled apparatus, the first request including the first authentication credentials and a unique identifier of the voice-enabled apparatus. The method further includes authenticating, at the vendor backend server, the first user account using the first authentication credentials and the unique identifier of the voice-enabled apparatus and linking the first user account to the voice-enabled apparatus, and receiving, at a user interface associated with the voice-enabled apparatus and operated by the user, a second request to link the first user account with a second user account, the second request including second authentication credentials associated with a second user account at the provider. The method further includes transmitting, by the user interface to a provider backend server of the provider, a request to authenticate the second user account at the voice-enabled apparatus, the request including the second authentication credentials, and authenticating, at the provider backend server of the provider, the second user account and linking the first user account to the second user account at the voice-enabled apparatus. The method further includes receiving an input audio signal from the user at the microphone unit of the voice-enabled apparatus, and determining, by the processor, that the second audio signal includes vocal attribute data associated with the user. The method further includes, determining, by the processor, that the second audio signal includes a portion of speech associated with a command to execute a requested functionality of the voice-assisted member interface, and validating, that the vocal attribute data matches the voice biometric profile associated with the user. The method further includes transmitting, by the processor to the provider backend server, the command to execute the requested functionality of the voice-assisted member interface, and validating, at the provider backend server, that the command from the voice-enabled apparatus is associated with an active account at the provider. The method further includes in response to the vocal attribute data matching the voice biometric profile and the command from the voice-enabled apparatus being associated with an active account at the provider, executing, by the provider backend server, the requested functionality of the voice-assisted member interface, generating, by the provider backend server, a response for the user and transmitting the response to the voice-enabled apparatus, and outputting, at the speaker, an output audio signal associated with the response.

In some embodiments, the method further includes receiving an audio input signal from a user at the microphone unit of the voice-enabled apparatus, converting, at the voice-enabled apparatus, the audio input signal to a computer readable text format, transmitting, from the voice-enabled apparatus to the vendor server, the converted audio input signal, and determining, by the vendor server, whether the converted audio input signal includes a request for a service provider search and one or more search criteria. The method may further include in response to the converted audio input signal including a request for a service provider search and one or more search criteria, determining whether a provider backend server of a provider includes an associated application programming interface, wherein the provider is separate and distinct from the vendor. The method may further include in response to determining that the provider backend server does include an associated application programming interface, transmitting the one or more search criteria to the associated application programming interface of the provider backend server. The method may further include executing, by the provider backend server, a database search in a database in communication with the provider backend server, based on the one or more search criteria, the database storing a plurality of records corresponding to individual service providers associated with the second provider. The method may further include generating, by the provider backend server, a list of search results including a subset of records, of the plurality of records stored on the database, the subset of records matching the one or more search criteria. The method may further include transmitting, from the provider backend server, to the vendor server, the list of search results, generating, from the vendor server a response based on the list of search results and transmitting the response to the voice-enabled apparatus, and outputting, at the speaker, an audio output signal associated with the response.

In some embodiments, the method further includes in response to determining that the provider backend server does not include an associated application programming interface, transmitting, from the vendor server, to the provider backend server, a request for the plurality of records corresponding to individual service providers. The method may further include in response to receiving the request for the plurality of records, transmitting, from the provider backend server to the vendor server, the plurality of records, and executing, by the vendor server, a search of the plurality of records, based on the one or more search criteria. The method may further include generating, by the vendor server, the list of search results including the subset of records, of the plurality of records received from the provider backend server, the subset of records matching the one or more search criteria, generating, from the vendor server a response based on the list of search results and transmitting the response to the voice-enabled apparatus, and outputting, at the speaker, an audio output signal associated with the response.

BRIEF DESCRIPTION OF THE SEVERAL VIEWS OF THE DRAWINGS

The following detailed description of embodiments of the system and method for virtual assistant enhanced access of private information, will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

Figure 1:
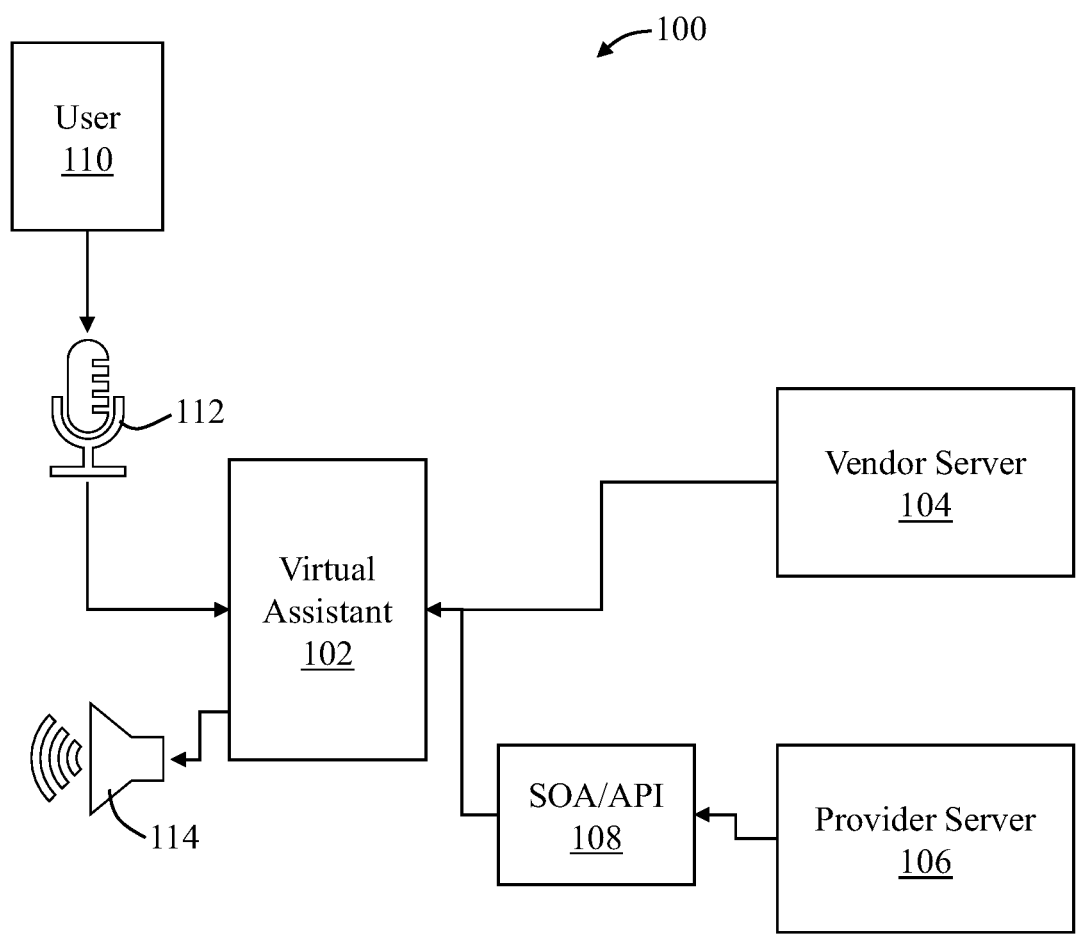
FIG. 1 is a block diagram illustrating an implementation of a system for virtual assistant enhanced access of private information in accordance with an exemplary embodiment of the present disclosure.

Numerous details are described herein in order to provide a thorough understanding of the example embodiment illustrated in the accompanying drawings. However, some embodiments may be practiced without any of the specific details, and the scope of the claims is only limited by those features and aspects specifically recited in the claims. Furthermore, well-known methods, components, and circuits have not been described in exhaustive detail so as not to unnecessarily obscure pertinent aspects of the embodiments described herein.

Some embodiments of the present disclosure provide improvements to existing voice enabled virtual assistant devices by providing a system configured to provide users of the voice enabled virtual assistant device on-demand secure access to their protected personal and identifying information. For ease of reference, and without limiting any of the foregoing, at least some aspects of the invention will be described in the health care field. The system may be configured to create a relationship between accounts associated with the voice enabled virtual assistant device and a healthcare provider using authentication methods such that a user may request their protected health information (PHI) via the voice enabled virtual assistant device. Referring to the drawings in detail, wherein like reference numerals indicate like elements throughout, there is shown in FIG. 1 a system for virtual assistant enhanced access of private information, in accordance with an exemplary embodiment of the present disclosure.

Referring to FIG. 1, there is shown a block diagram illustrating an implementation of a system for virtual assistant enhanced access of private information, generally designated 100. While some example features are illustrated, various other features have not been illustrated for the sake of brevity and so as not to obscure pertinent aspects of the example embodiments disclosed herein. To that end, as a non-limiting example, the system for virtual assistant enhanced access of private information 100, referred to herein as system 100, may include one or more computing devices in communication with one or more networked servers. In one embodiment, the system 100 comprises a virtual assistant enabled device 102, a vendor server 104 in communication with the virtual assistant enabled device 102, and a provider server 106 in communication with the virtual assistant enabled device 102.

The virtual assistant enabled device 102 may be a computing device configured to receive a user input (e.g., voice commands from a user 110) and provide an output in response to the user input. The virtual assistant enabled device 102, referred to herein as the virtual assistant 102, may be one or more computing devices having stored thereon executable code for performing tasks in response to commands (e.g., spoken) from a user 110. The virtual assistant enabled device 102 may include one or more processors and/or one or more memory units configured to store and execute executable code for performing the virtual assistant tasks. The virtual assistant 102 may be a smart phone, smart speaker, a computer, a laptop computer, a tablet device, a netbook, an internet kiosk, a personal digital assistant, a mobile phone, a gaming device, or any other computing device. In some embodiments, the virtual assistant 102 includes an audio input device 112 (e.g., a microphone) and an audio output device 114 (e.g., a speaker). In some embodiments, one or more of the audio input device 112 and/or audio output device 114 are integrated with the virtual assistant 102 (e.g., a smart speaker having an integrated microphone and/or speaker). In some embodiments, one or more of the audio input device 112 and/or audio output device 114 are external to the virtual assistant (e.g., headphones connected to a smartphone).

In some embodiments, the virtual assistant 102 may be connected to or include a graphical display screen (e.g., touch screen, LED screen, LCD screen) for displaying outputs to a user. In some embodiments, the virtual assistant 102 may include one or more light sources (e.g., an LED light source) configured to emit a light in response to receiving data from one or more external servers. For example, the light source may emit a light in response to receiving updated information from one or more external servers relating to the user of the virtual assistant 102. In this manner the virtual assistant 102 may be configured to display a visual indication to the user that information has been received which pertains to the user. In some embodiments, the virtual assistant 102 is a device that is compliant with the Health Insurance Portability and Accountability Act (HIPAA) standards for protected health information. In some embodiments, the virtual assistant 102 is a device that is compliant with one or more data protection and/or privacy standards, such as for example, but not limited to, the General Data Protection Regulation (GDPR), the Act on the Protection of Personal Information (APPI), and the Data Protection Act.

In some embodiments, the virtual assistant 102 is a device configured to be operated by a user 110 using spoken commands. In some embodiments, the virtual assistant 102 is configured to recognize a plurality of spoken commands (also referred to as utterances). For example, a user 110 may speak phrases such as "what is the weather", "listen to jazz", "what is my schedule", which the virtual assistant 102 is configured to recognize. In some embodiments, the virtual assistant 102 is configured to perform tasks associated with the spoken commands. For example, in response to a spoken command from a user 110 asking "what is the weather", the virtual assistant 102 may execute computer executable code for determining weather information (e.g., the temperature) pertaining to the location of the user 110. The virtual assistant 102 may then return the output of the task to the user 110 audibly and/or visually. For example, the virtual assistant 102 may send a signal to the audio output device 114 causing the audio output device 114 to play an audible message including the temperature and weather forecast for the user 110 to hear. It will be understood that not all possible spoken commands and corresponding tasks performed by virtual assistant 102 will be listed for sake of brevity.

In some embodiments, the executable code used to perform tasks may be included in one or more software applications. In some embodiments, the virtual assistant 102 is configured to perform tasks included in a voice-assisted member interface. A voice-assisted member interface may refer to a collection of computer executable code developed to be either freely distributed or sold by an entity other than the original vendor of the virtual assistant 102. For example, in the above example, the virtual assistant 102 was shown to be capable of retrieving weather information and returning it to a user 110. This functionality may be performed by a collection of computer executable code developed by a vendor of the virtual assistant 102. A voice-assisted member interface may be installed on the virtual assistant 102 such that one or more functionalities is added to the virtual assistant 102. For example, a user 110 may install a voice-assisted member interface for ordering food from a specific restaurant in their local area. The user 110 may provide a spoken command to "order a pepperoni pizza from Joe's" causing the virtual assistant 102 to execute computer executable code included in said voice-assisted member interface to submit an order for a pepperoni pizza at Joe's. The virtual assistant 102 may have a plurality of voice-assisted member interface packages installed thereon each of which being configured to allow the voice-assisted member interface to perform specific functionalities. In some embodiments, the voice-assisted member interface packages may be developed by parties or entities that are not the vendor of the virtual assistant 102 (e.g., a third-party developer).

In some embodiments, the virtual assistant 102 may be in communication with a vendor server 104 associated with a vendor of the virtual assistant 102. In some embodiments, the vendor server 104 is configured to provide a plurality of optional software applications (e.g., voice-assisted member interfaces, software applications developed by the vendor) for installation and use on the virtual assistant 102. In some embodiments, the vendor server 104 may include one or more servers and/or one or more databases for storing data related to users 110 of the virtual assistant 102. In some embodiments, the vendor server 104 may store data relating to a plurality of user accounts (also referred to as vendor specific accounts), each user account being associated with a user 110 of the virtual assistant 102. For example, a first user may have a vendor specific account with corresponding data stored on the vendor server 104 and a second user may have a different vendor specific account with corresponding data stored on the vendor server 104. The data corresponding to a vendor specific account may include information about the user 110 such as: user specific voice biometric data, user authentication credentials (e.g., password, username, PIN), the name of the user, and any other information about the user.

In some embodiments, the virtual assistant 102 is configured to associate a user 110 with their associated vendor specific account via one or more authentication means. In some embodiments, the authentication means may include a personal identification number (PIN), voice authentication and/or a password. In some embodiments, the user 110 may provide one or more of the authentication means to virtual assistant 102 such that the user 110 is authenticated with their associated vendor specific account. In some embodiments, the user 110 may be required to be authenticated with their vendor specific account (e.g., logged in to their vendor specific account) in order to access the functionalities of the virtual assistant 102. In some embodiments, the virtual assistant 102 may require that a user 110 be authenticated with their associated vendor specific account before the user 110 is able to access, enable, and/or use the functionality of the virtual assistant 102. For example, one or more functionalities included in software applications provided by the vendor, a third-party and/or the voice-assisted member interface may be accessible via the virtual assistant 102 following user 110 being authenticated with their vendor specific account. In some embodiments, virtual assistant 102 may be configured to authenticate a user 110 by performing voice biometric authentication. In some embodiments, virtual assistant 102 may be configured to authenticate a user 110 if voice biometric authentication and a valid PIN are provided by the user 110.

In some embodiments, the virtual assistant 102 may be configured to be used by one or more users 110, each having a different associated vendor account. In some embodiments, the virtual assistant 102 may be configured to compare the vocal attributes of the user 110 to the voice biometric data stored on the vendor server 104 in order to distinguish between different users 110. For example, a first user may speak a voice command to virtual assistant 102 and the virtual assistant may compare the vocal attributes of the received voice command to voice biometric data associated with the first user's vendor specific account to determine whether the voice command was generated by the first user.

In some embodiments, the virtual assistant 102 may be in communication with a provider server 106 associated with a provider having one or more voice-assisted member interfaces configured to be installed on the virtual assistant 102. In some embodiments, the provider may be an entity other than the vendor of the virtual assistant 102. In some embodiments, the provider may be a healthcare provider and/or an entity which provides health insurance. In some embodiments, the provider server 106 may be one or more servers and/or databases having stored thereon data associated with a plurality of provider accounts. In some embodiments, a user 110 of the virtual assistant 102 may have an associated provider account as well as the vendor specific account. In some embodiments, the data associated with a provider account may include protected health information specific to a user 110. For example, the provider server 106 may store data such as: an insurance policy, insurance premiums, primary care providers, user's medical history information, healthcare benefits, prescription medication information, healthcare related appointments, healthcare benefit plan information (e.g., HSA, HRA, HSA+, HRA+, FSA, and LPFSA), user information (e.g., name, age, weight, height, gender, address), and any other information relating to the user and/or the user's healthcare. In some embodiments, the provider server 106 may store data indicating whether a user 110 has a valid insurance policy provided by the provider server. In some embodiments, the provider server 106 may store healthcare data not specific to any one user 110. For example, the provider server 106 may store data relating to a listing of healthcare providers which are a part of the providers healthcare network, a healthcare glossary including definitions of healthcare and healthcare insurance related terms.

In some embodiments, a user 110 may be required to provide authentication credentials before the user can access their protected health information associated with their provider account. In some embodiments, the voice-assisted member interface installed on virtual assistant 102 may be configured to authenticate a user 110 with their associated provider account using one or more of voice biometrics, authentication credentials specific to the provider account, and/or a PIN. In some embodiments, the voice-assisted member interface may be configured to create an association between a user's provider account and vendor specific account. In some embodiments, the virtual assistant 102 may be configured to provide access to a user's 110 protected health information, provided the user's 110 provider account and vendor specific account are associated with one another.

Figure 2A:
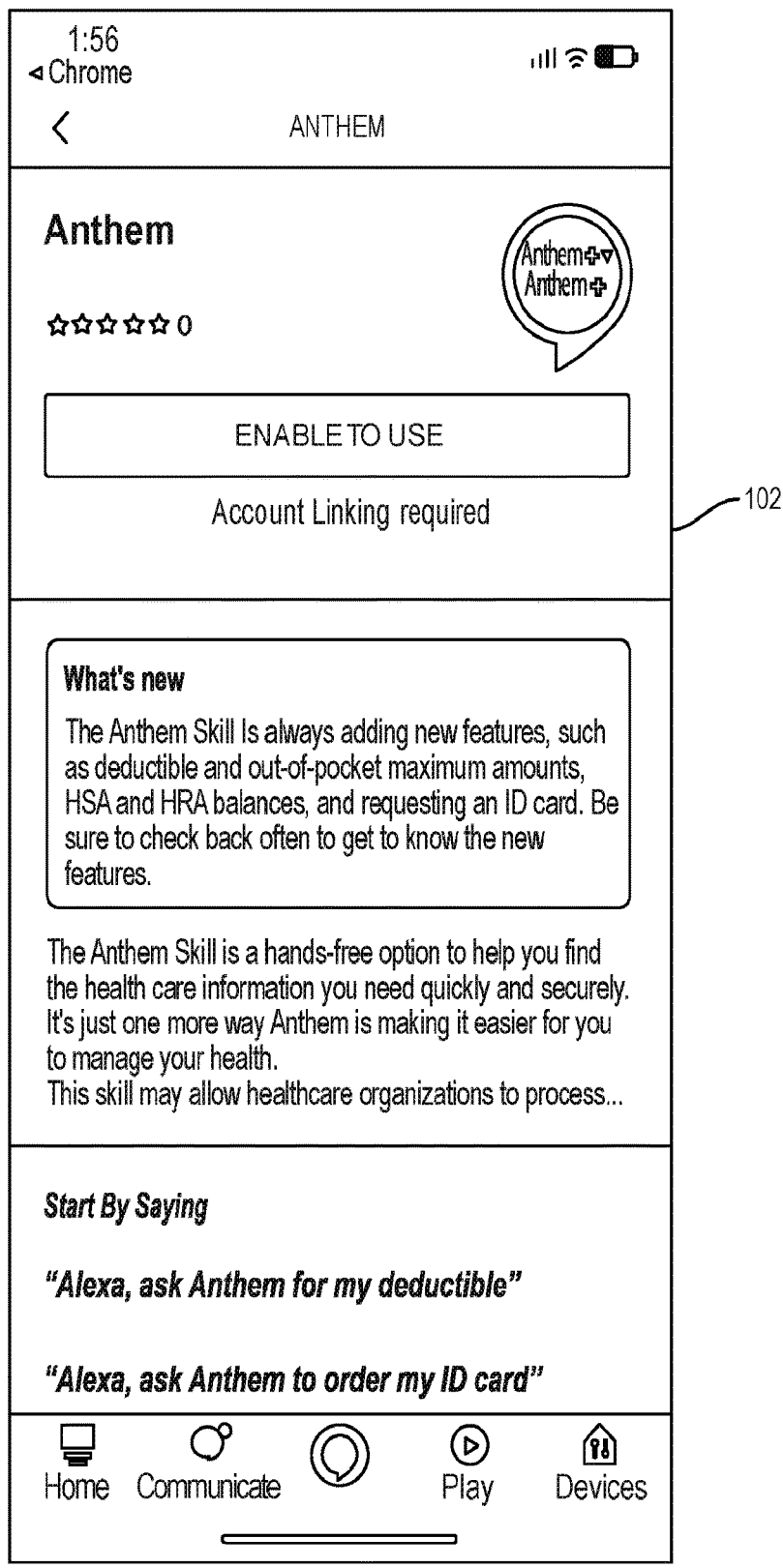
FIGS. 2A-2F illustrate exemplary user interfaces displayed on the virtual assistant for establishing an association between a vendor specific account and a provider account, according to an embodiment of the present disclosure.
Figure 2B:
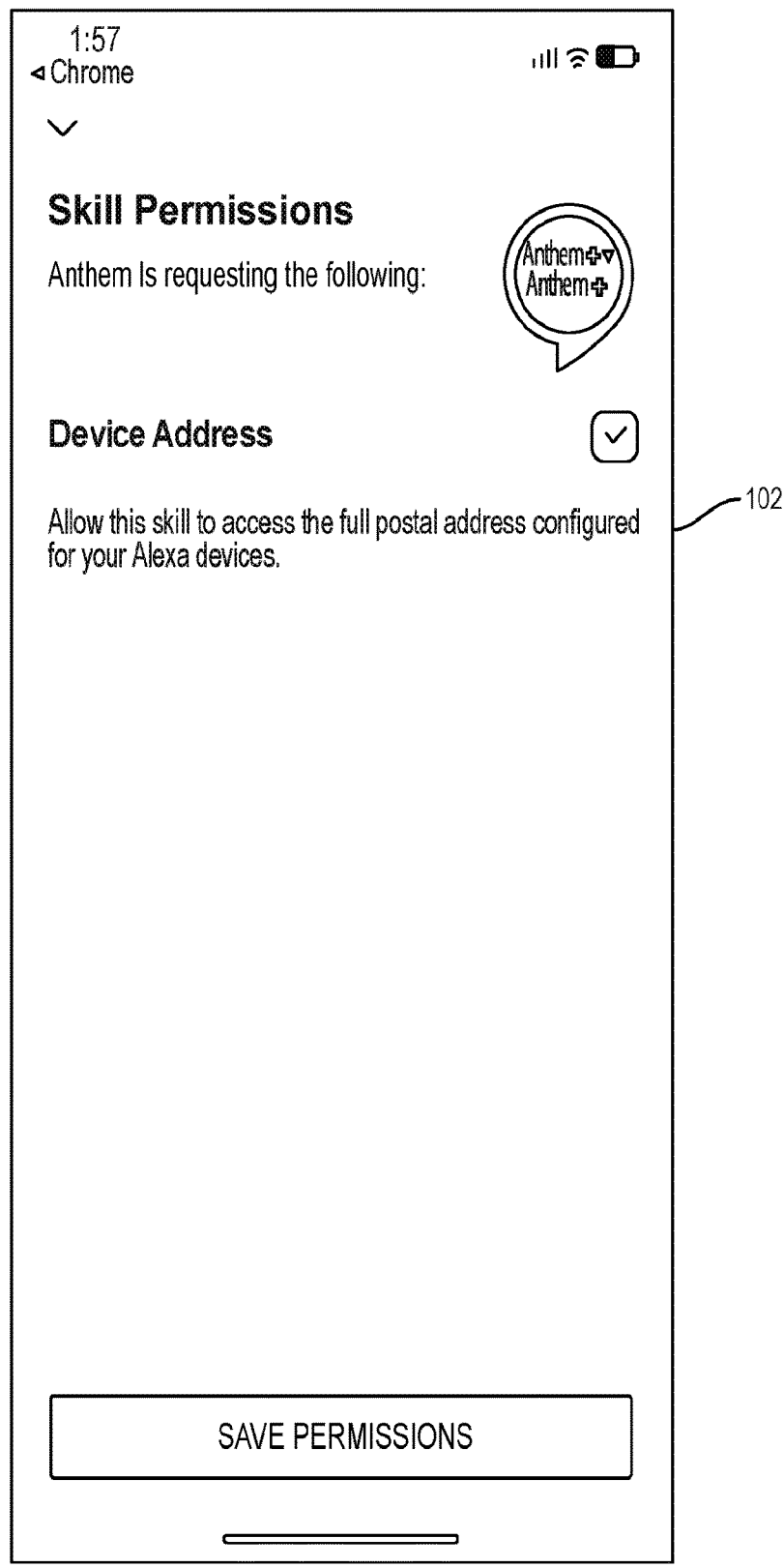
Figure 2C:
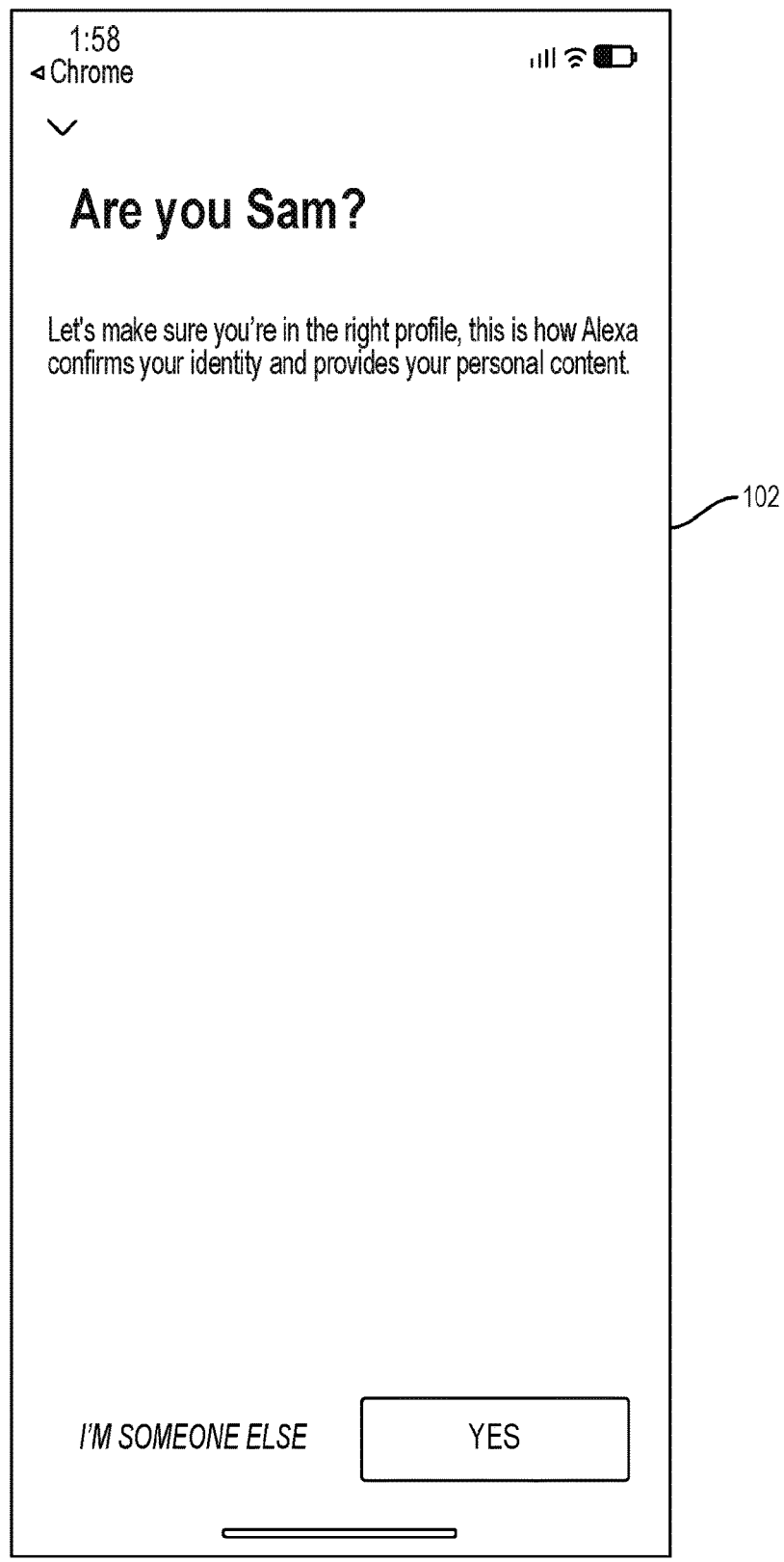
Figure 2D:
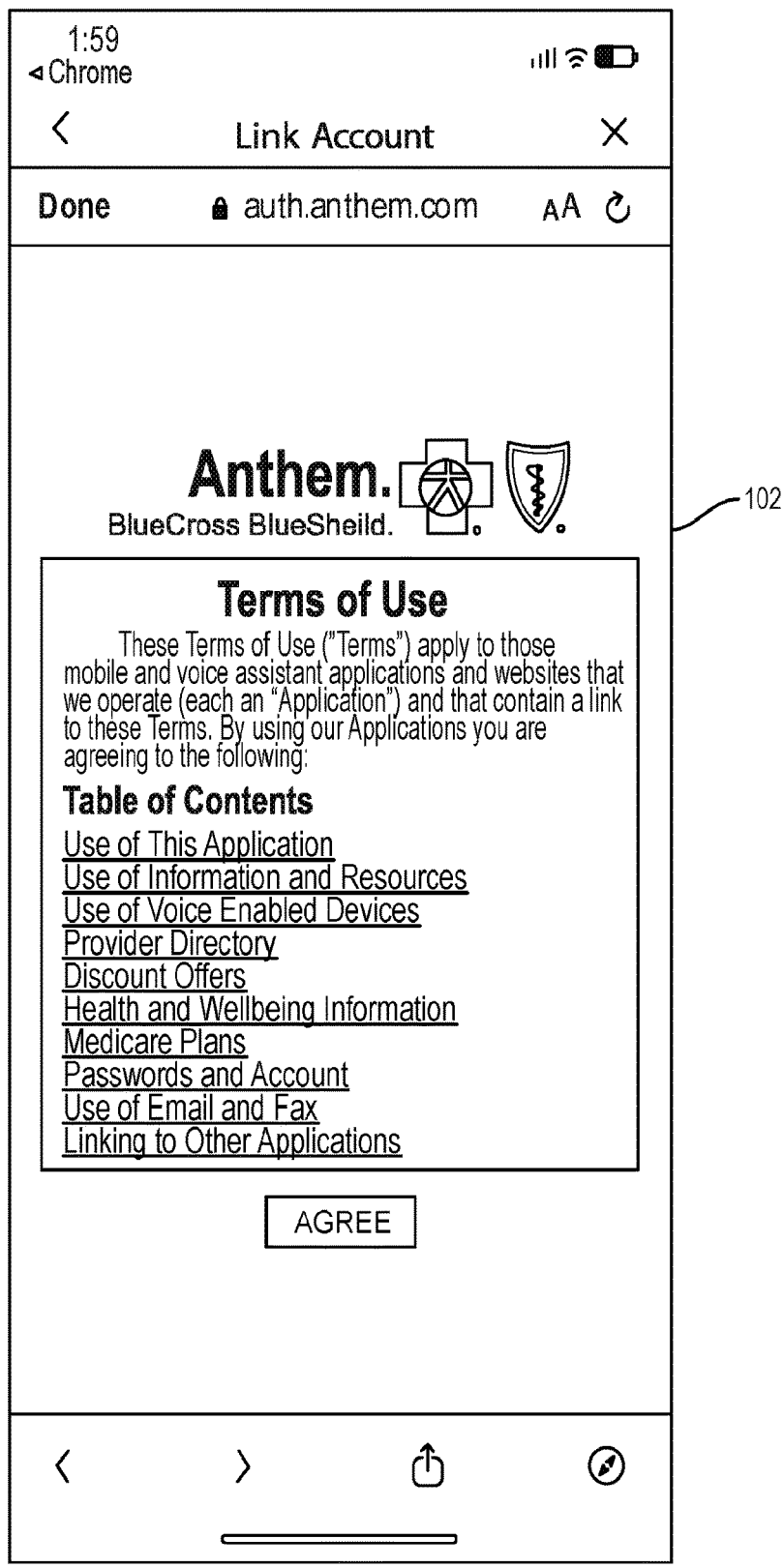

Referring to FIGS. 2A-2F, there is shown exemplary user interfaces displayed on the virtual assistant 102 associated with a method of establishing an association between a vendor specific account and a provider account, according to an embodiment of the present disclosure. In some embodiments, the user-interfaces illustrated in FIGS. 2A-2F are displayed on a display screen, or a portion thereof, of a device that is external to, or separate from, the virtual assistant 102, but that is in communication with the virtual assistant 102. For example, the user-interfaces illustrated in FIGS. 2A-2F may be displayed on a smartphone that is in communication with the virtual assistant (e.g., a smart speaker). In some embodiments, when the voice-assisted member interface is activated for the first time on the virtual assistant 102, the user 110 may be required to, via the virtual assistant 102, establish an association (also referred to as a link herein) between the user's 110 provider account and vendor specific account. The user-interfaces (UIs) illustrated in FIGS. 2A-2F are displayed on a smartphone which has the virtual assistant 102 installed thereon, it will be understood though that the virtual assistant 102 may be any other computer device (e.g., a smart speaker). In some embodiments, the virtual assistant 102 may be configured to require that the voice-assisted member interface be enabled in order for the user 110 to access the functionality of the voice-assisted member interface via the virtual assistant 102. For example, as shown in FIG. 2A, the virtual assistant 102 displays to the user 110 a user interface for allowing the user 110 to enable the voice-assisted member interface (e.g., the user 110 provides an input at the "Enable to Use" button). In some embodiments, the virtual assistant 102 be configured to display a user interface for providing the user 110 with a selection of one or more permissions for data requested by the voice-assisted member interface. For example, as shown in FIG. 2B, the virtual assistant 102 displays a user interface which provides the user 110 with a display of the data requested by the voice-assisted member interface, in this example the full postal address associated with the virtual assistant. The user 110 is able to, via the user interface displayed in FIG. 2B, select whether or not to allow the voice-assisted member interface access to said data.

In some embodiments, the virtual assistant 102 may be configured to display a user interface for verifying the identity of the user 110. For example, referring to FIG. 2C, the virtual assistant 102 displays to the user 110 (e.g., Sam), a user interface which requests that the user 110 confirm that the name displayed on the screen is the user's name. In this example, the user 110 is already authenticated with (e.g., logged in to) their vendor specific account on the virtual assistant 102. In some embodiments, the virtual assistant 102 may be configured display a user interface requesting that the user 110 authenticate with a vendor specific profile. For example, if the user 110 is not authenticated with a vendor specific profile, the user interface displayed in FIG. 2C may request that the user 110 authenticate with a vendor specific profile before the user 110 is able to proceed to associate their vendor specific account with their provider account. In some embodiments, the virtual assistant 102 is configured to display a terms of use user interface to allow the user 110 to review the terms of use associated with the voice-assisted member interface. In some embodiments, the voice-assisted member interface is configured to cause the virtual assistant 102 to open a web browser on a user device for displaying the terms of use associated with the voice-assisted member interface. For example, referring to FIG. 2D, the virtual assistant 102 opens a web-browser on the user's 110 smartphone which displays the terms of use for the user 110 to review. In some embodiments, the user 110 must agree to the terms of use before proceeding to associate their vendor specific account with their provider account.

In some embodiments, the virtual assistant 102 may be configured to display a user interface requesting that a user 110 provide authentication credentials associated with their provider account. For example, referring to FIG. 2E, the virtual assistant 102 displays a user interface which displays input fields for the user's 110 username and password. The user 110 may input their authentication credentials (e.g., the username and password associated with their provider account) via the user interface displayed by the virtual assistant. In some embodiments, the virtual assistant 102 may be configured to validate whether the user input authorization credentials are valid. For example, the voice-assisted member interface may include executable code which causes the virtual assistant 102 to transmit the authorization credentials to the provider server 106. The provider server 106 may be configured to determine whether the user input authorization credentials are valid and transmit a signal to the virtual assistant indicating whether the authorization credentials are valid. In some embodiments, in response to receiving a signal from the provider server 106 that the authorization credentials are valid, the virtual assistant 102 may display a user interface indicating that the provider account and vendor specific account have been successfully associated. For example, referring to FIG. 2F, the virtual assistant 102 displays to the user a user interface indicating that the provider account and vendor specific account have been linked.

Figure 3A:
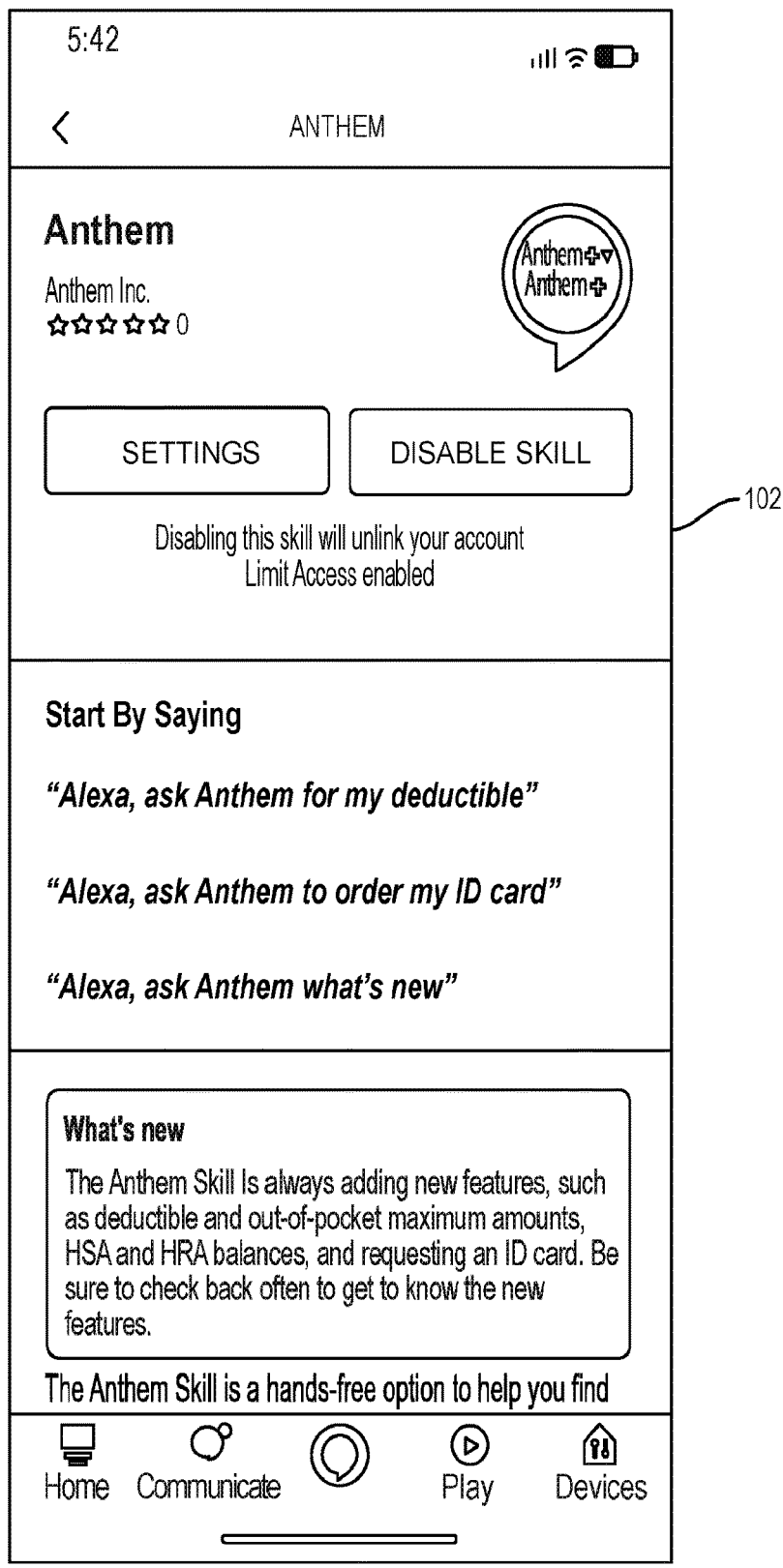
FIGS. 3A-3F illustrate exemplary user interfaces displayed by the virtual assistant associated with a method of creating voice biometric data.
Figure 3B:
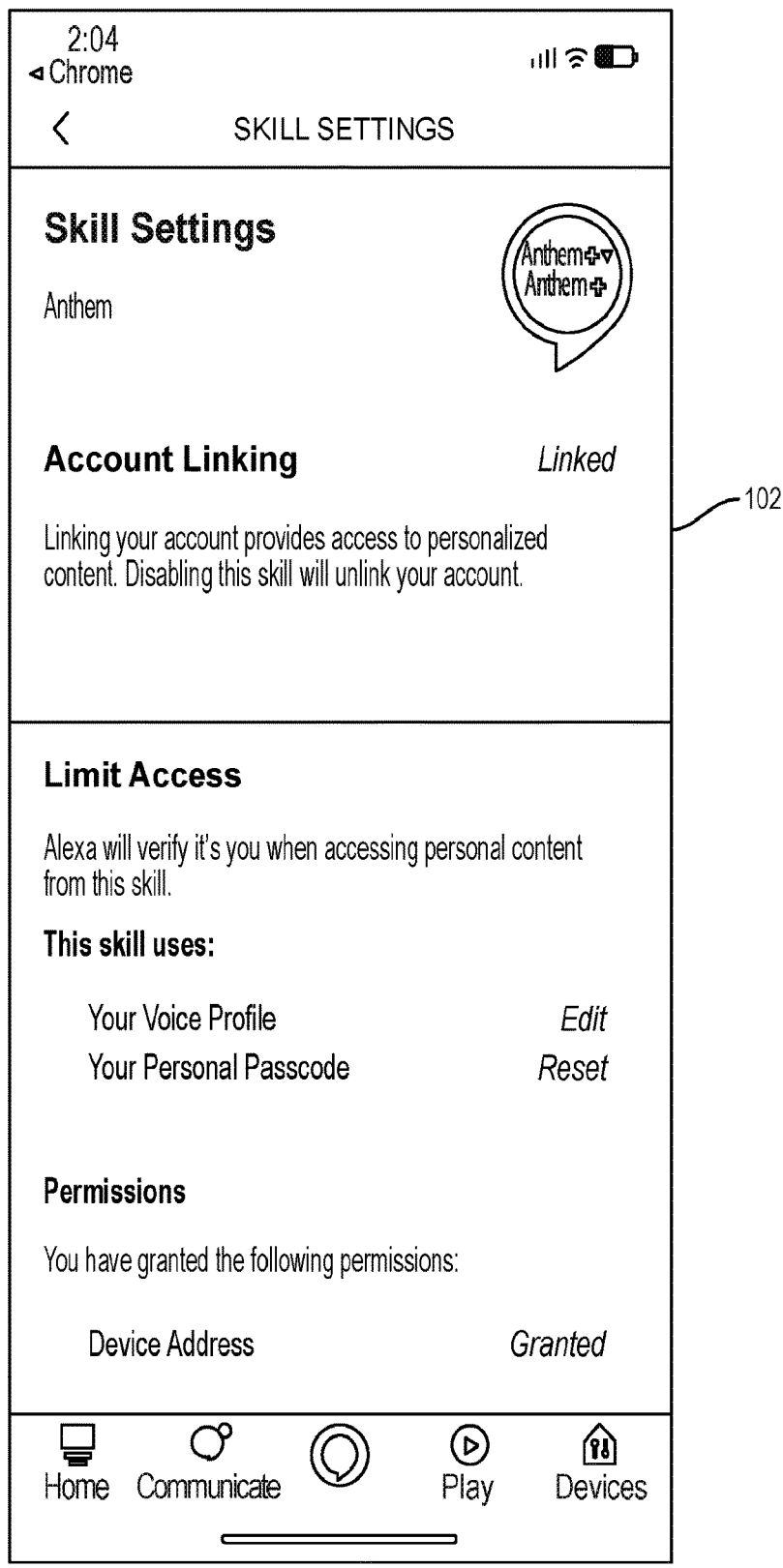
Figure 3C:
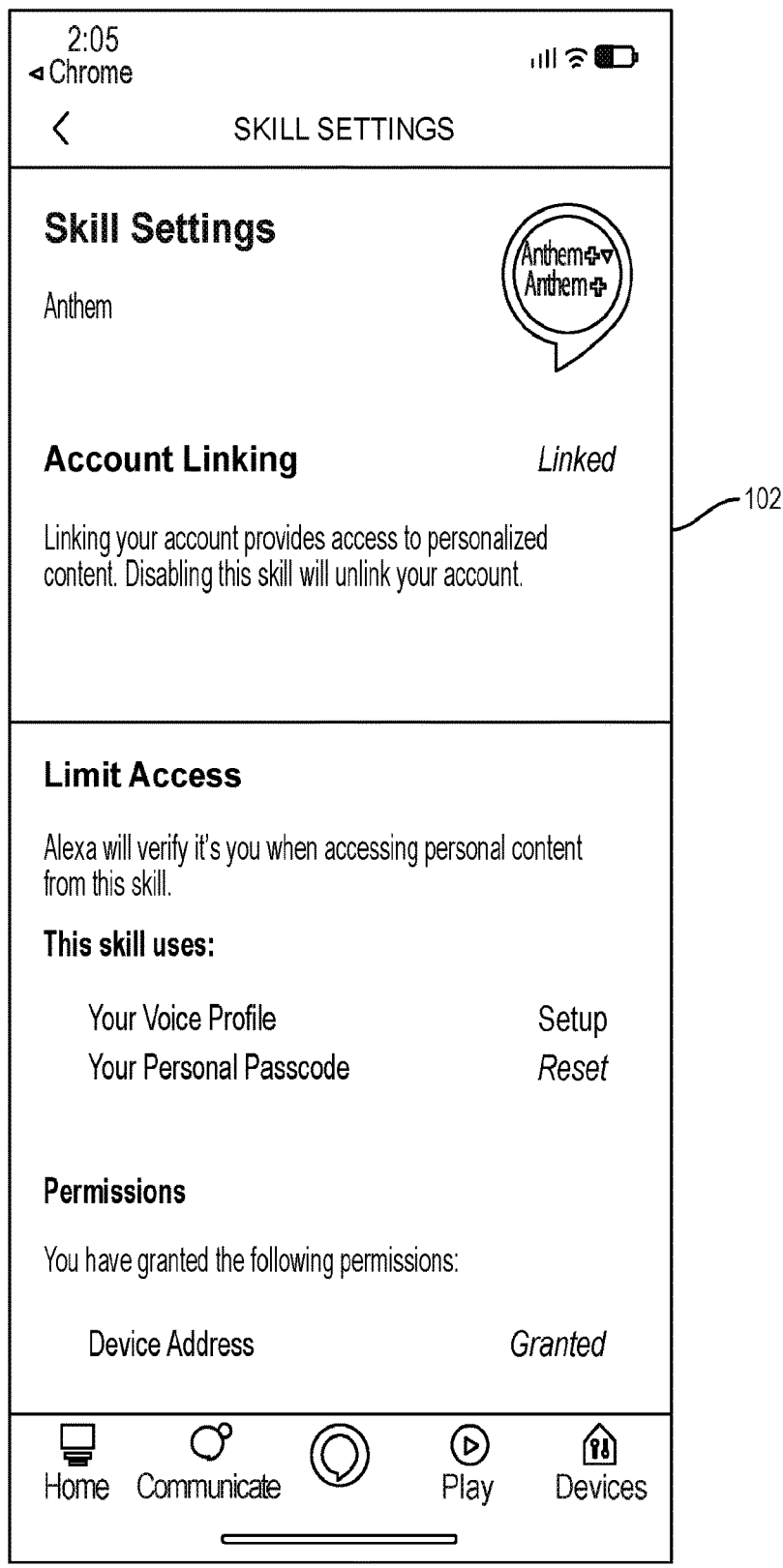

In some embodiments, the voice-assisted member interface may include executable code configured to determine whether voice biometric data exists for the user 110 of the virtual assistant 102. In some embodiments, if voice biometric data does not exist, the virtual assistant 102 may require that the user 110 perform a series of steps to create voice biometric data. Referring to FIGS. 3A-3F, there is shown exemplary user interfaces displayed by the virtual assistant associated with a method of creating voice biometric data. In some embodiments, the user-interfaces illustrated in FIGS. 3A-3F are displayed on a display screen, or a portion thereof, of a device that is external to, or separate from, the virtual assistant 102, but that is in communication with the virtual assistant 102. For example, the user-interfaces illustrated in FIGS. 3A-3F may be displayed on a smartphone that is in communication with the virtual assistant (e.g., a smart speaker). The virtual assistant 102, may be configured to display a user interface for providing a user 110 access to the settings of the voice-assisted member interface and/or disabling the voice-assisted member interface. For example, as shown in FIG. 3A, the virtual assistant displays a user interface which includes user interacable buttons for accessing the settings of the voice-assisted member interface and disabling the voice-assisted member interface. In some embodiments, the virtual assistant 102 may be configured to direct the user to a settings user interface associated with the voice-assisted member interface. In some embodiments, the settings associated with the provider account may include the voice biometric data associated with their vendor specific account. In some embodiments, the settings user interface may provide an indication as to whether the voice biometric data exists. For example, as shown in FIG. 3B, the settings user interface displays that the voice profile (e.g., the voice biometrics) can be edited, indicating that voice biometric data exists which is associated with the user's 110 vendor specific account. Alternatively, as shown in FIG. 3C, the settings user interface may display that the voice profile can be created, or set up, indicating that voice biometric data associated with the user's 110 vendor specific account does not exist. In some embodiments, the voice-assisted member interface may require that voice biometric data associated with the user's 110 vendor specific account exist before the user 110 is able to use at least some of the functionality of the voice-assisted member interface via the virtual assistant.

Figure 3D:
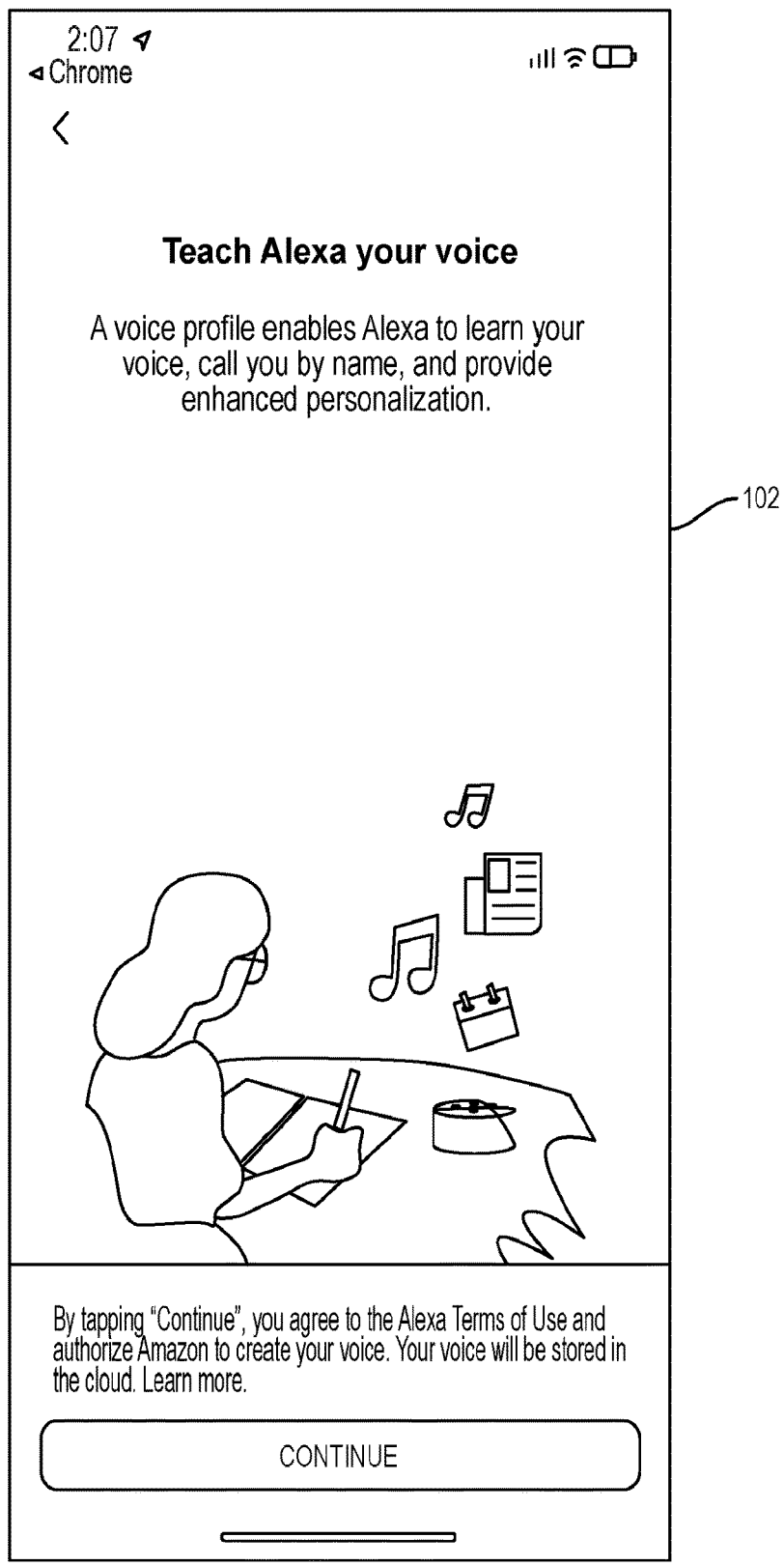
Figure 3E:
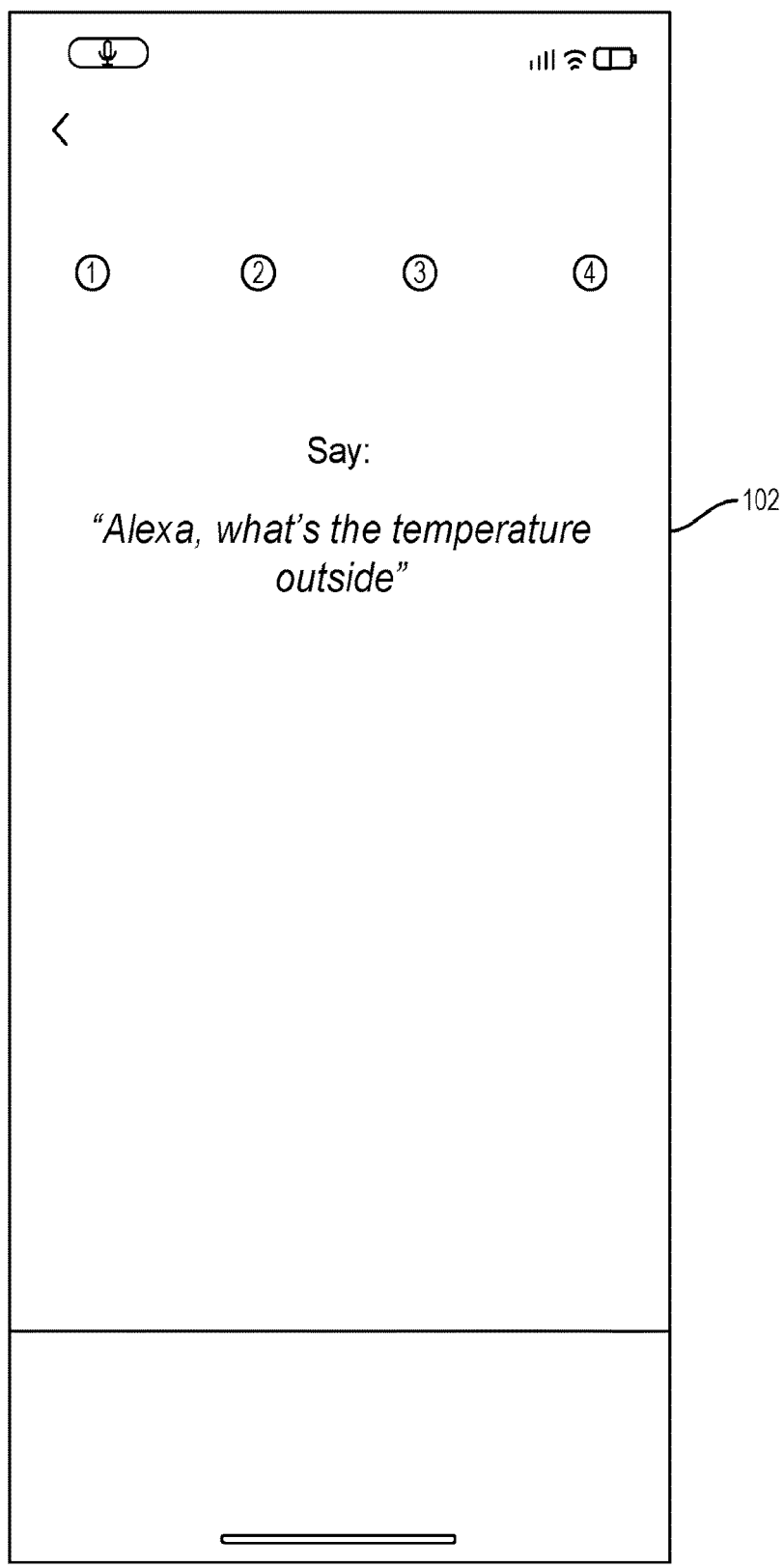
Figure 3F:
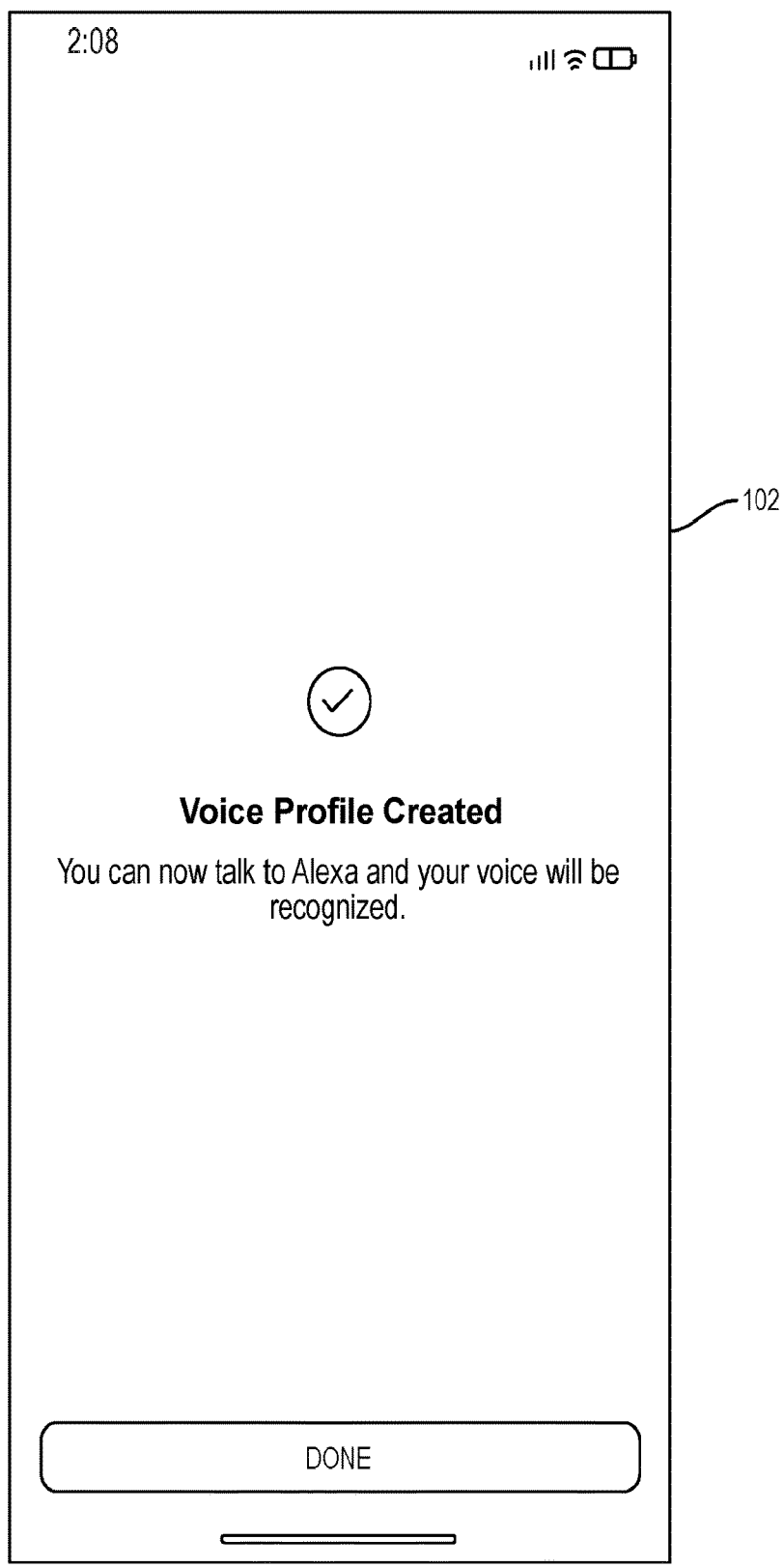

Referring to FIGS. 3D-3F, there is shown exemplary user interfaces, displayed by the virtual assistant, for creating voice biometric data. In some embodiments, the virtual assistant 102 may receive an input from the user 110 indicating that the user 110 wishes to create voice biometric data. For example, the user may press the "setup" text displayed in the user interface shown in FIG. 3C. In some embodiments, the virtual assistant 102 may be configured to display a user interface prompting the user 110 to start a voice biometric setup process. In some embodiments, the virtual assistant 102 may be configured to display a user interface prompting the user 110 to speak one or more phrases. For example, referring to FIG. 3E, the virtual assistant 102 may display a first prompt requesting that the user say "what is the temperature outside". The user 110 may speak the requested phrase and the virtual assistant 102 may be configured to receive the spoken phrase via the audio input device 112 connected to the virtual assistant 102. The virtual assistant 102 may be configured to determine that the spoken phrase matches the requested phrase. If the spoken phrase matches the requested phrase, the virtual assistant 102 may prompt the user 110 to speak one or more additional phrases until voice biometric data can be generated. In some embodiments, once the user 110 has provided a pre-determined amount of spoken phrases (e.g., four phrases), the virtual assistant 102 may be configured to generate voice biometric data. In some embodiments, the generated voice biometric data is transmitted from the virtual assistant 102 to the vendor server 104. In some embodiments, the vendor server 104 may associate the voice biometric data with the user's 110 vendor specific account and store the voice biometric data for later retrieval. In some embodiments, the virtual assistant 102 may be configured to display a user interface indicating whether voice biometric data was successfully created. For example, referring to FIG. 3F, the virtual assistant 102 may display a user interface which includes text that the voice profile was created. In some embodiments, the association of the provider account with the vendor specific account may not be complete until voice biometric data associated with the vendor specific account is stored on vendor server 104.

Figure 4:
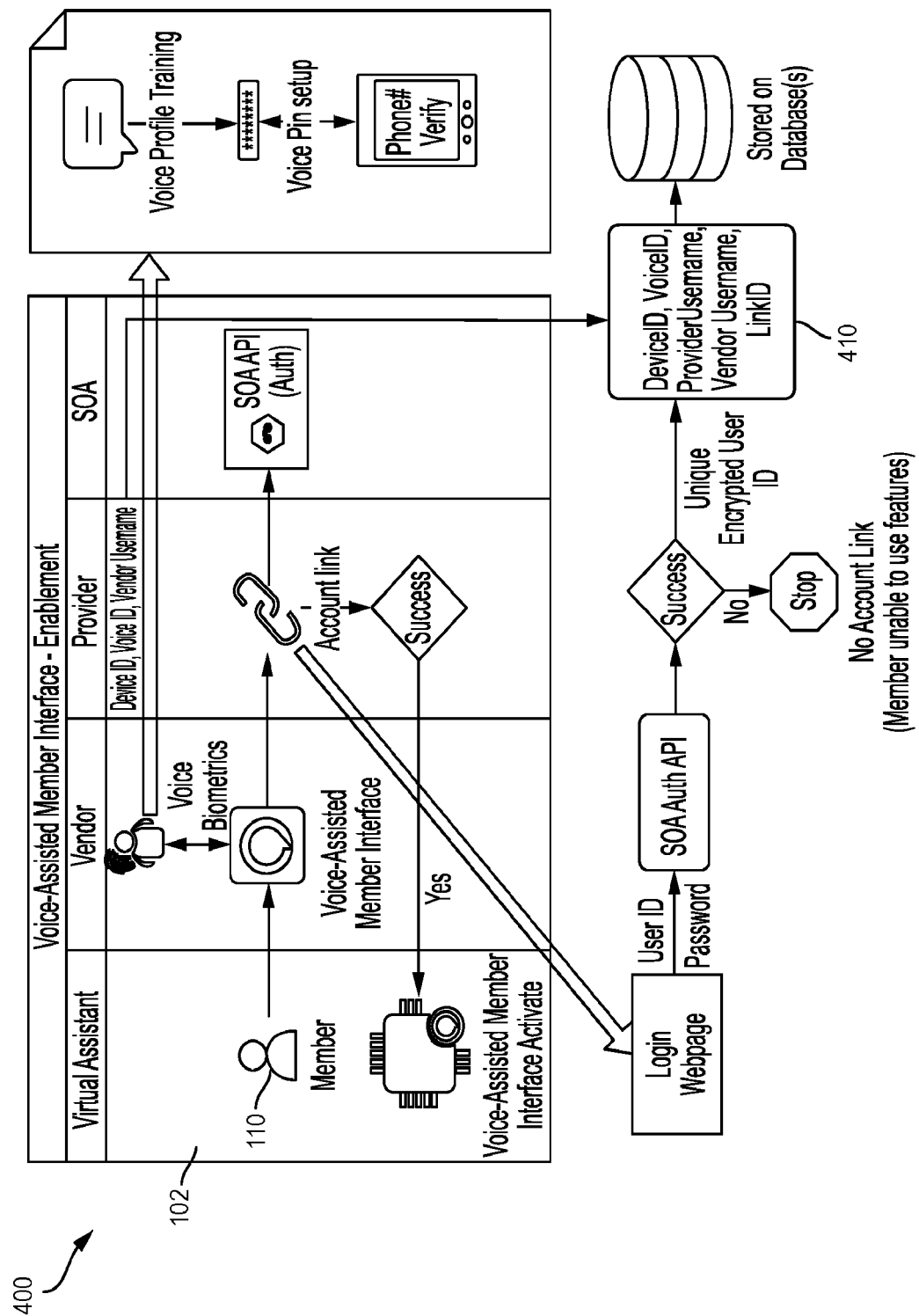
FIG. 4 illustrates an exemplary diagram depicting a method of associating a first account with a second account.

Referring to FIG. 4, there is shown an exemplary diagram depicting a method of associating a first account with a second account in accordance with an exemplary embodiment of the present disclosure.

In some embodiments, prior to the method 400, virtual assistant 102 may transmit first credentials, input by user 110, to vendor server 104 to authenticate the virtual assistant 102 with the user's vendor specific account. Put another way, prior to the method 400, the user 110 may already be authenticated with their vendor specific account via the virtual assistant 102. In some embodiments, the method 400 may include a user (e.g., user 110) installing a voice-assisted member interface on a voice-enabled virtual assistant device (e.g., virtual assistant 102). In some embodiments, the voice-assisted member interface may be downloaded from a server hosted by a vendor of the virtual assistant 102 (e.g., vendor server 104).

In some embodiments, the method 400 may include requesting access to voice biometric data stored on the vendor server 104. In some embodiments, service oriented architecture (SOA) and/or an application programming interface (API) is used by the voice-assisted member interface to cause the virtual assistant 102 to request and receive voice biometric data from the vendor server 104 and/or the provider server 106. In some embodiments, the method 400 includes receiving at the virtual assistant 102, the requested voice biometric data. In some embodiments, the voice biometric data is associated with a first account. In some embodiments, the first account is a vendor specific account associated with user 110. In some embodiments, the method 400 includes in response to no voice biometric data being associated with the first account, transmitting a request from the vendor server 104 to the virtual assistant 102 to create voice biometric data. For example, the vendor server 104 and/or virtual assistant 102 may be configured to determine that no voice biometric data exists for a user 110 having an associated vendor specific account and the virtual assistant 102 may display prompts to the user 110 to create voice biometric data as shown in FIGS. 3D-3F.

In some embodiments, the method 400 may include receiving an indication from the user 110 via the virtual assistant 102, that the user 110 wishes to enable the voice-assisted member interface. For example, the user 110 selecting to enable the voice-assisted member interface via the user interface displayed in FIG. 2A. In some embodiments, the method 400 may include transmitting a request from the virtual assistant 102 to the provider server (e.g., provider server 106) to associate the first account with a second account associated with the provider (e.g., the provider account). The association of the first account (e.g., the vendor specific account) with a second account (e.g., a separate account) may alternatively be referred to as account linking.

Figure 2E:
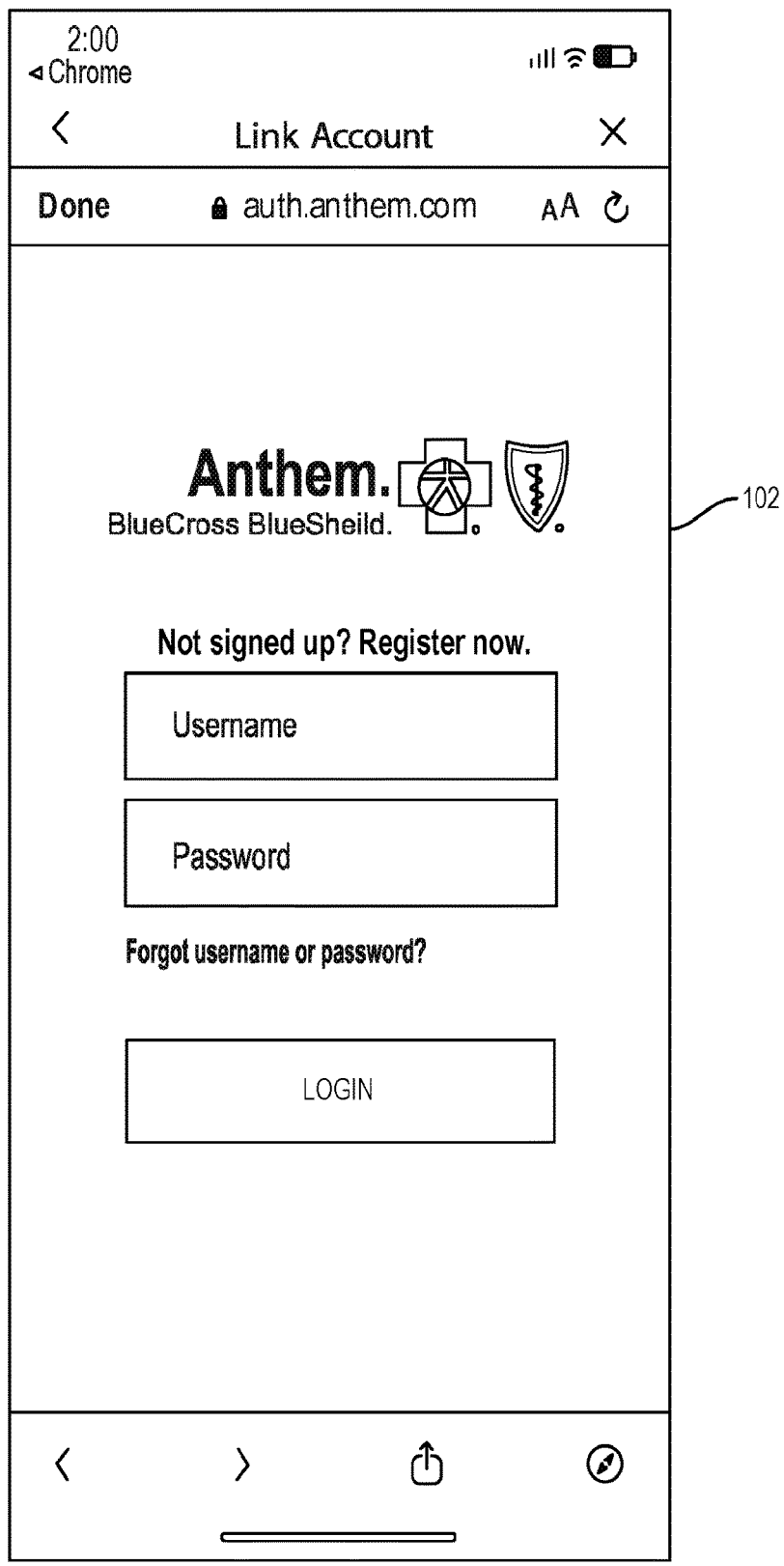
Figure 2F:
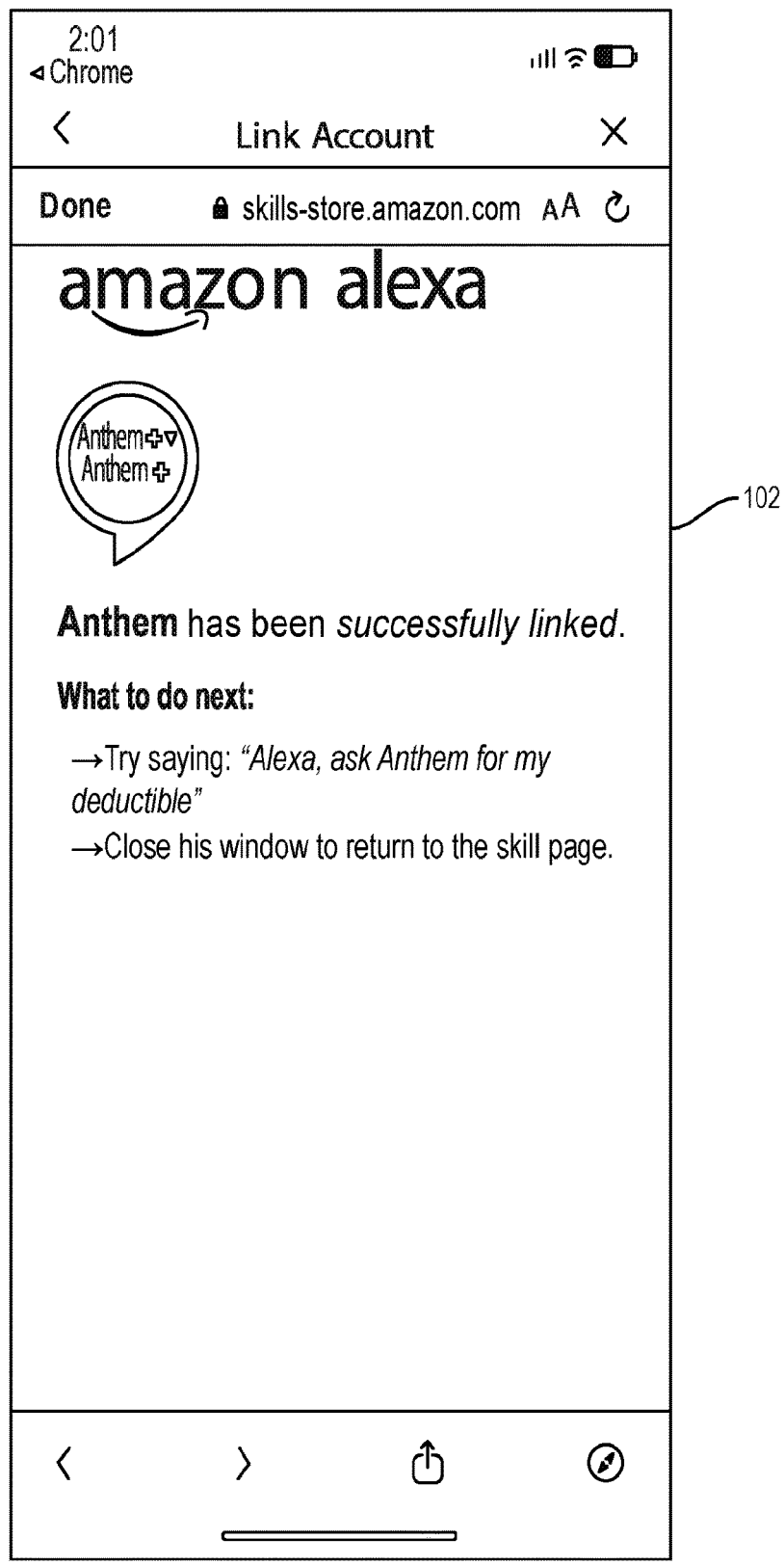

In some embodiments the method 400 may include, transmitting from the provider server 106 to the virtual assistant 102, a request for one or more authentication credentials associated with a second account (e.g., provider account). For example, the virtual assistant 102 may display a user interface (e.g., login webpage) which prompts the user 110 to input their username and password associated with their provider account as shown in FIG. 2E. Alternatively, the user may be directed to a login webpage separate from the virtual assistant 102 where the user may input their authentication credentials. In some embodiments, the method 400 may include, receiving and transmitting the one or more authentication credentials (e.g., from the virtual assistant 102, from the device used to access the login webpage) to the provider server 106.

In some embodiments, the method 400 may include validating at the provider server 106, that the received authentication credentials are valid by comparing the received credentials to data associated with a provider account associated with the user 110. For example, the provider server 106 may be configured to determine that the received credentials match credentials for a provider account, specific to the user 110, having data stored on the provider server 106. In some embodiments, the provider server 106 may utilize a SOA or API interface without backend computing components to authenticate the user as described herein.

In response to the credentials being valid, the method 400 may include generating an authorization token 410 indicating that the association of the provider account and the vendor account is valid. Generation of the authorization token 410 may include generating a unique identifier associated with the association of the provider and vendor accounts (e.g., the account linking). For example, a "linkID", also referred to as a link identifier, may be generated that is a unique random identifier. In some embodiments, the link identifier is encrypted. The authorization token may be an electronic key that enables the user 110 to authenticate and prove the successful association of their first and second accounts. The authorization token may include one or more unique identifiers specific to the association of the user's vendor specific and provider specific accounts. For example, the authorization token 410 may include the user's vendor specific username, provider specific username, a device identifier, a voice identifier, and the generated link identifier. The user's vendor specific username may be the username that is associated with the user's vendor specific account. The provider specific username may be the username that is associated with the user's provider specific account. The device identifier (e.g., "deviceID") may be a unique ID specific to the user's virtual assistant 102 and may be generated by the vendor server 104. The voice identifier (e.g., "voiceID") may be a unique ID specific to the user's voice biometric data and may be generated by the vendor server 104. In some embodiments, one or more of the user's vendor specific username, provider specific username, device identifier, voice identifier, and generated link identifier are encrypted. In response to the credential input by the user 110 not being valid, the method 400 may terminate and no association, or account link, between the first account and second account may occur.

In some embodiments, the authorization token, including the vendor username, provider username, deviceID, voiceID, and/or linkID, is stored on one or more databases. For example, the authorization token may be stored on a first database associated with the vendor of the virtual assistant 102 and a second database associated with the provider and/or the voice-assisted member interface. For example, the authorization token may be stored on a first database accessible by the vendor server 104 and a second database accessible by the voice-assisted member interface. In embodiments, where the provider is not the host and/or developer of the voice-assisted member interface, the authorization token may still be stored on a database associated with the host and/or developer of the voice-assisted member interface. In this manner, when the user 110 requests a functionality of the voice-assisted member interface via the virtual assistant 102, the authorization tokens, stored on the first and second databases may be compared to one another to validate the association of the user's vendor specific and provider specific accounts.

In some embodiments, the authorization token is stored on the provider server 106. In some embodiments, the authorization token may be stored on at least one of the vendor server 104, provider server 106, and the virtual assistant 102, or any combination thereof. The authorization token may be used when the user 110 attempts to access functionality of the voice-assisted member interface in order to authenticate the user 110. For example, the authorization tokens, stored on the first and second databases, may be compared, in response to a user requesting functionality of the voice-assisted member interface. The voice-assisted member interface, via the virtual assistant 102, may perform the comparison of the authorization tokens in order to validate that the authorization tokens match. In some embodiments, the provider server 106 and/or vendor server 104 may validate the authorization tokens. In response to the authorization token being valid, the voice-assisted member interface may be configured to allow access to the requested functionality via the virtual assistant 102.

In response to the credentials being valid the method 400 may include transmitting from the provider server 106 to the virtual assistant an indication that the authentication credentials are valid. In some embodiments, the method 400 may include creating an association between the first account (e.g., the vendor specific account) and the second account (e.g., the provider account). In some embodiments, the association between the vendor specific account and provider account may only occur the first time a user 110 requests to activate the voice-assisted member interface. In some embodiments, the provider server 106 and associated provider need not be a developer and/or owner of the voice-assisted member interface. For example, the voice-assisted member interface may be developed and/or owned by a party A and the account linking may be performed between a user's accounts with parties B and C, that are separate and distinct from party A.

In some embodiments, in response to the first account being associated with the second account, the virtual assistant 102 may be configured to enable the voice-assisted member interface such that the functionalities of the voice-assisted member interface are available to the user 110. In some embodiments, one or more of the functionalities of the voice-assisted member interface may include the transmission of protected health information to the virtual assistant 102. In some embodiments, the virtual assistant 102 may be configured to require one or more authentication processes when execution one or more functionalities included in the voice-assisted member interface is requested by a user 110. For example, the virtual assistant 102 may be configured to perform voice biometric authentication based on the spoken command received from the user 110. In some embodiments, the virtual assistant 102 is configured to perform voice biometric authentication and require the user provide another form of authentication (e.g., a PIN) before the virtual assistant 102 retrieves the requested information from the provider server 106. In some embodiments, if at least one form of authentication (e.g., voice biometrics, PIN) is not valid (e.g., user's voice doesn't match the voice biometric data, PIN is incorrect) the virtual assistant 102 may be configured to not retrieve the requested information from the provider server 106.

In some embodiments, when a user 110 requests a functionality of the voice-assisted member-interface via virtual assistant 102, the voice-assisted member interface, via the virtual assistant 102, may transmit a request to the provider server 106 to determine the validity of the authorization token generated during the account linking of method 400. In some embodiments, the authorization token must be valid in order for the voice-assisted member interface to provide any functionality to the user 110 via the virtual assistant 102. In some embodiments, the virtual assistant 102 may be configured to, via the voice-assisted member interface, require voice-biometric and/or another form of authentication as well as the authorization token being valid. For example, the authorization token may need to be valid and the voice-biometric data may need to match the voice-biometric data associated with the account of the user 110.

In this manner, the voice-assisted member interface may be configured to cause the virtual assistant 102 to communicate with the vendor server 104 and provider server 106 to determine voice-biometric validity and authorization token validity prior to providing access to the one or more functionalities of the voice-assisted member interface. Various functionalities are described herein and it will be understood that authorization token validation, and, in some embodiments, one or more other forms of authentication have been performed and that said validation and/or authentication was successful prior to the execution of said functionality.

In some embodiments, the first spoken command from a user 110 which is received by the virtual assistant 102 requesting a functionality of the voice-assisted member interface be performed may initiate the start of a session. The virtual assistant 102 at the start of the session may be configured to require that voice biometric authentication is successful and that a user input PIN is valid as described above. The virtual assistant 102 may perform the requested functionality of the voice-assisted member interface and request input from the user 110 indicating whether the user wishes to continue the session. For example, the user 110 may provide a spoken command requesting in-network deductibles for medical benefits based on the user's 110 associated insurance plan. The virtual assistant 102 may output the requested information and output (via audio, visual, or a combination thereof) a message asking if the user 110 would like to continue. If the user 110 wishes to use another functionality of the voice-assisted member interface, via the virtual assistant 102, the user 110 may respond with a spoken command indicating they wish to continue. A subsequent spoken command, uttered within a pre-determined amount of time from the user's indication they wish to continue the session, that would cause functionality of the voice-assisted member interface to be performed by the virtual assistant 102 would be within the same session. In some embodiments, the virtual assistant 102 may be configured to perform functionalities of the voice-assisted member interface in response subsequent spoken commands provided within the same session without performing the authentication methods described above (voice biometrics and PIN). In other embodiments, the virtual assistant 102 is configured to perform one or more of voice biometric authentication and PIN authentication in response to each spoken command from the user 110 which would cause the virtual assistant 102 to perform a functionality of the voice-assisted member interface.

Figure 5A:
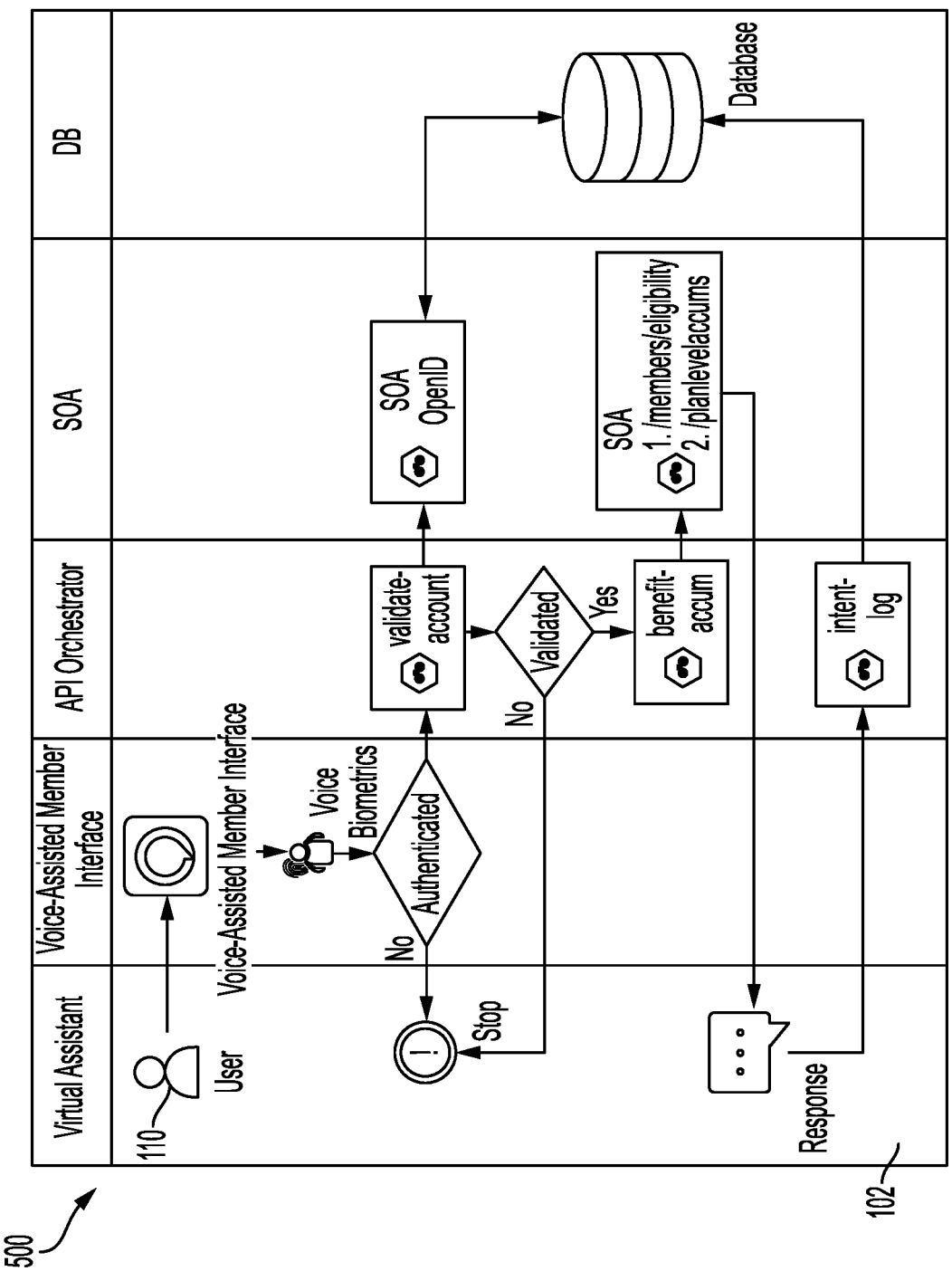
FIG. 5A illustrates an exemplary diagram depicting a method of securely transmitting information to a voice-enabled virtual assistant device from a provider server.

Referring to FIG. 5A, there is shown an exemplary flowchart depicting an exemplary method of securely transmitting information to a voice-enabled virtual assistant device from a provider server. In some embodiments, the user 110 may provide an input (e.g., a spoken command) to a voice-enabled virtual assistant device (e.g., virtual assistant 102) requesting information related to the user's associated provider account. The requested information may be protected health information that is stored on a database included in the provider server 106. For example, a user 110 may input a command (e.g., spoken command) at the virtual assistant 102 to receive information relating to healthcare benefits offered by the provider.

In some embodiments, the method 500 includes, in response to the command from the user 110, performing a voice biometric authentication based on the spoken command received from the user, at the virtual assistant 102. In some embodiments, the virtual assistant 102 also displays a request which indicates that the user's PIN is required to authenticate the user 110. In some embodiments, the method 500 includes determining, whether the authentication is valid. For example, the virtual assistant 102 may compare the spoken command to voice biometric data and received PIN associated with the user's 110 vendor specific account and determine if the voice biometrics and PIN are correct. If one or more of the PIN and voice biometrics are incorrect, the method 500 may end and the virtual assistant 102 may be configured to display a message to the user 110 that authentication failed.

In some embodiments, if the authentication is valid, the method 500 may include validating the user's provider account. For example, the voice-assisted member interface may utilize a SOA or API to query a database associated with the provider server 106 to determine if the user 110 has a valid policy associated with their provider account. If the account is not validated, the method 500 may end and the virtual assistant 102 may be configured to display a message to the user 110 indicating that account validation failed. If the account is validated, the method 500 may include transmitting a request, from the virtual assistant 102 to the provider server 106 for the requested health benefits information. In some embodiments, the method 500 may include transmitting the requested information from the provider server 106 to the virtual assistant 102 and outputting the requested information via the virtual assistant.

In some embodiments, depending on the requested information, the output from the virtual assistant 102 may include an indication as to where the user 110 may go to access the requested information. For example, a user 110 may request a list of healthcare notifications which may include protected health information and the virtual assistant 102 may output a message directing the user 110 to access a secure website associated with the provider to access the information. In some embodiments, the output may include a prompt to the user 110 to perform a subsequent user action (e.g., a subsequent user input).

In some embodiments, the virtual assistant 102 may be configured to determine, based on data associated with the provider account, if there is a gap or deficiency in healthcare for the user 110. A gap in healthcare may refer to a situation in which there is a discrepancy between healthcare actions associated with a user's provider account and predetermined clinical quality metrics. In some embodiments, the virtual assistant 102 may be configured to provide an output notifying a user 110 of a gap in healthcare associated with the user's provider account. For example, the virtual assistant 102 may output a message (e.g., visual and/or audible) which notifies the user 110 that there is a gap in their healthcare. In some embodiments, the virtual assistant 102 may be configured to provide time-specific outputs based on time-specific healthcare records stored on provider server 106. In some embodiments, the virtual assistant 102 may output a message (e.g., visual and/or audible) in response to detecting that the date and/or time overlap with or are within a predetermined amount of time from a range of dates. For example, if the current date, detected by the virtual assistant 102, overlaps with flu season, the virtual assistant 102 may output a message reminding a user 110 to receive a flu shot.

In some embodiments, the method 500 may include creating a record of the spoken command in a database included in the provider server 106.

Figure 5B:
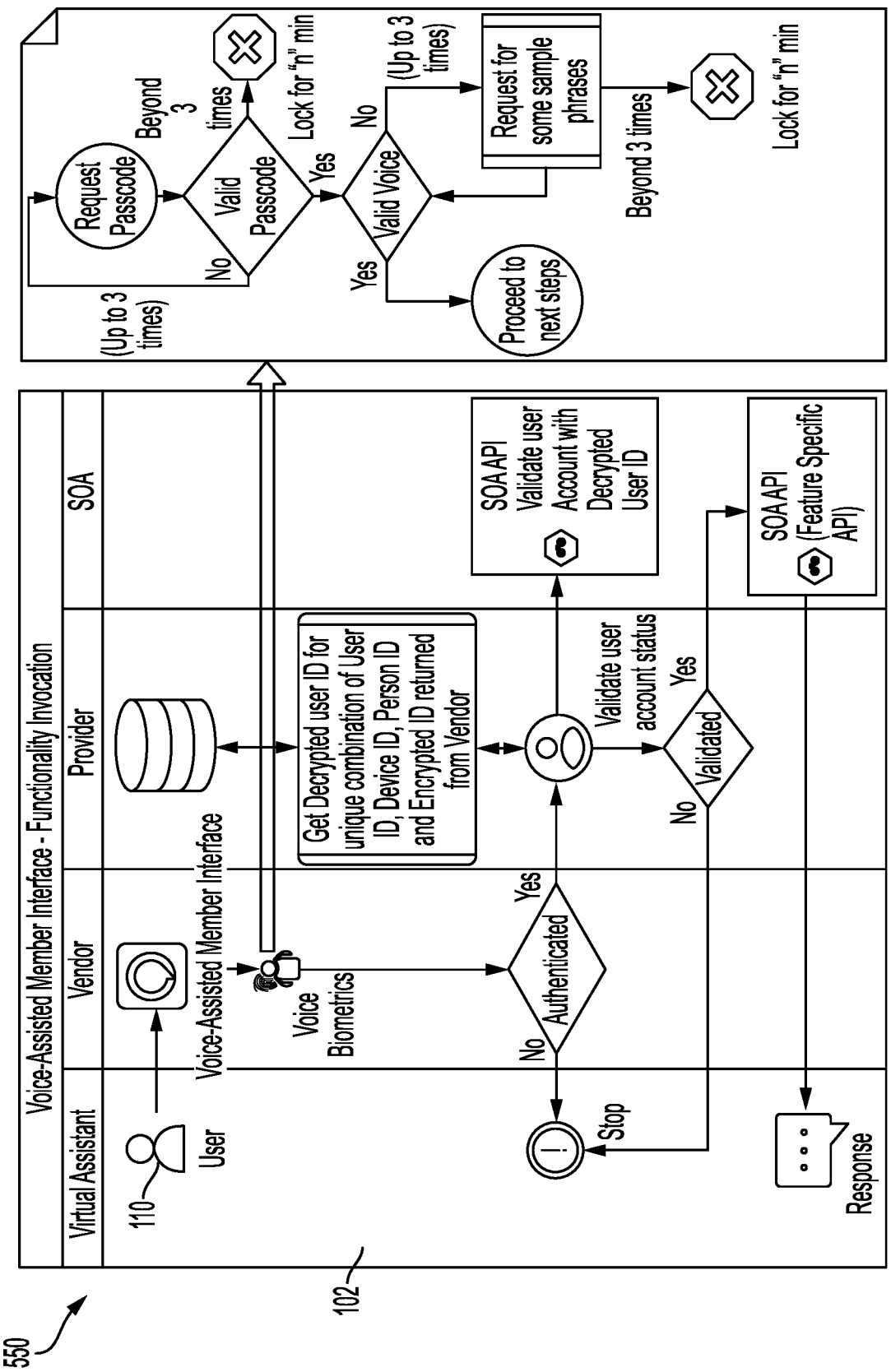
FIG. 5B illustrates an exemplary diagram depicting a method of invoking a functionality of the voice-assisted member interface.

Referring to FIG. 5B, there is shown a method 550 of invoking the functionality of the voice-assisted member interface. The method 500 may include receiving an input (e.g., a spoken command), from the user 110, requesting one or more functionalities of the voice-assisted member interface. The input may be received at the virtual assistant 102 and, in response to receiving the input from the user 110, the voice-assisted member interface may cause the virtual assistant 102 to communicate with the vendor server 104 to validate voice biometric data. The validation of the voice biometric data may include transmitting from the vendor server 104 to the virtual assistant 102, a request for a passcode. The passcode may be a PIN or other form of password that is known only to the valid user of the vendor specific account (e.g., the first account). Put another way, the PIN may be a PIN that is set up by the user 110 for their vendor specific account. In some embodiments, the user 110 is requested to audibly provide the PIN such that a two factor authentication takes place when the user 110 speaks their PIN to the virtual assistant 102. For example, by audibly providing the PIN, the voice assisted member interface may be configured to confirm that the PIN (e.g., a series of numbers, letters, phrases) matches the PIN associated with the user's vendor specific account and a voice biometric authentication may be performed. In this manner the PIN spoken by the user 110 may act as a form of two-factor authentication. The two-factor authentication as described above may be based on an information protection standard (e.g., HIPAA) and, therefore, it will be understood that under different information protection/privacy standards, there may be different requirements for authenticating a user prior to any protected information being transmitted to the virtual assistant 102 to be output to the user 110.

In some embodiments, the two-factor authentication is performed each time a different functionality of the voice-assisted member interface is requested by the user 110 at the virtual assistant 102. In other embodiments, the two-factor authentication is requested once within a continuous session. For example, the user 110 may request a first functionality (e.g., the user 110 requests their current deductible) and the two-factor authentication may be performed. The first functionality may be executed, as described in more detail below. Following the user's request for and execution of the first functionality, and within the same session, the user 110 may request a second functionality that may be different from the first functionality (e.g., scheduling a doctor visit). In response to the request for the second functionality, the voice-assisted member interface may, in some instances, not perform another two-factor authentication because it has already been performed within the same session. As such, the second functionality may proceed to be executed by the voice-assisted member interface.

The user may input the passcode and in response to the input passcode being correct, the voice biometrics of the spoken command may be compared to the voice biometric data stored on the vendor server 104. In response to the input passcode being incorrect, the user 110 may be presented with a predetermined number of retries (e.g., 3 retries) before the vendor server 104 blocks any further input attempts, for a period of time, and the method 550 is terminated. In response to voice biometric data not being valid/correct, the virtual assistant 102 may prompt the user to provide further audible input to validate the user's voice (e.g., speak sample phrases to the virtual assistant 102). The user 110 may be allowed a predetermined number of retries before the vendor server 104, for a period of time, blocks further retries and the method 550 is terminated.

In response to the voice biometric data and passcode being valid, the method 550 proceeds to validating the association of the first account (e.g., vendor specific account) and the second account (e.g., the provider specific account) corresponding to the user 110. Put another way, in response to the voice biometric data and passcode being valid, the method 550 may include validating the account link between the user's provider specific account and vendor specific account. For sake of brevity, the association of said accounts may be referred to as the account link. The voice-assisted member interface may be configured to cause the virtual assistant 102 and/or vendor server 104, or provider server 106, to validate the account link via the authorization tokens. The voice-assisted member interface, and/or the vendor or provider servers 104, 106, may compare the authorization tokens stored on the first and second databases as described above with reference to FIG. 4 that are created during the account linking method. For example, validating the authorization tokens may include retrieving said authorization token from a first database included in, or in communication with, the vendor server 104 and retrieving the authorization token from the second database included in, or in communication with the provider server 106. The authorization tokens may be compared, and in response to the authorization tokens (e.g., the Vendor Username, DeviceID, VoiceID, Provider Username, and LinkID) being a match, the association of the vendor and provider specific accounts (e.g., the account link) may be validated. In some embodiments, validating the authorization token includes, at the provider server 106, determining a decrypted user ID for the unique combination of Link ID, Device ID, Voice ID, Vendor Username, and/or Provider Username. The decrypted user ID may be used via an SOA API to validate the account link.

In response to the account link not being validated, the method 550 may terminate. In response to the account link being validated, the method 550 may include allowing the user access to one or more, or all, of the functionalities of the voice-assisted member interface and providing responses to any user requests after the user is validated. Some various functionalities are described herein with reference to FIGS. 5A, and 7-10B, however, it will be understood that the voice-assisted member interface may provide any number of functionalities, such as, but not limited to, conducting a search for a healthcare provider, provide health insurance deductible information, request a new insurance card be mailed to them, and scheduling a healthcare appointment. Although the above examples are limited to the healthcare industry, it will be understood that the functionalities enabled by the methods and systems described herein may apply to other industries in which access to protected or private information is required in order to perform a function or task. For example, some other industries may include, but are not limited to, personal finance and education.

Figure 6A:
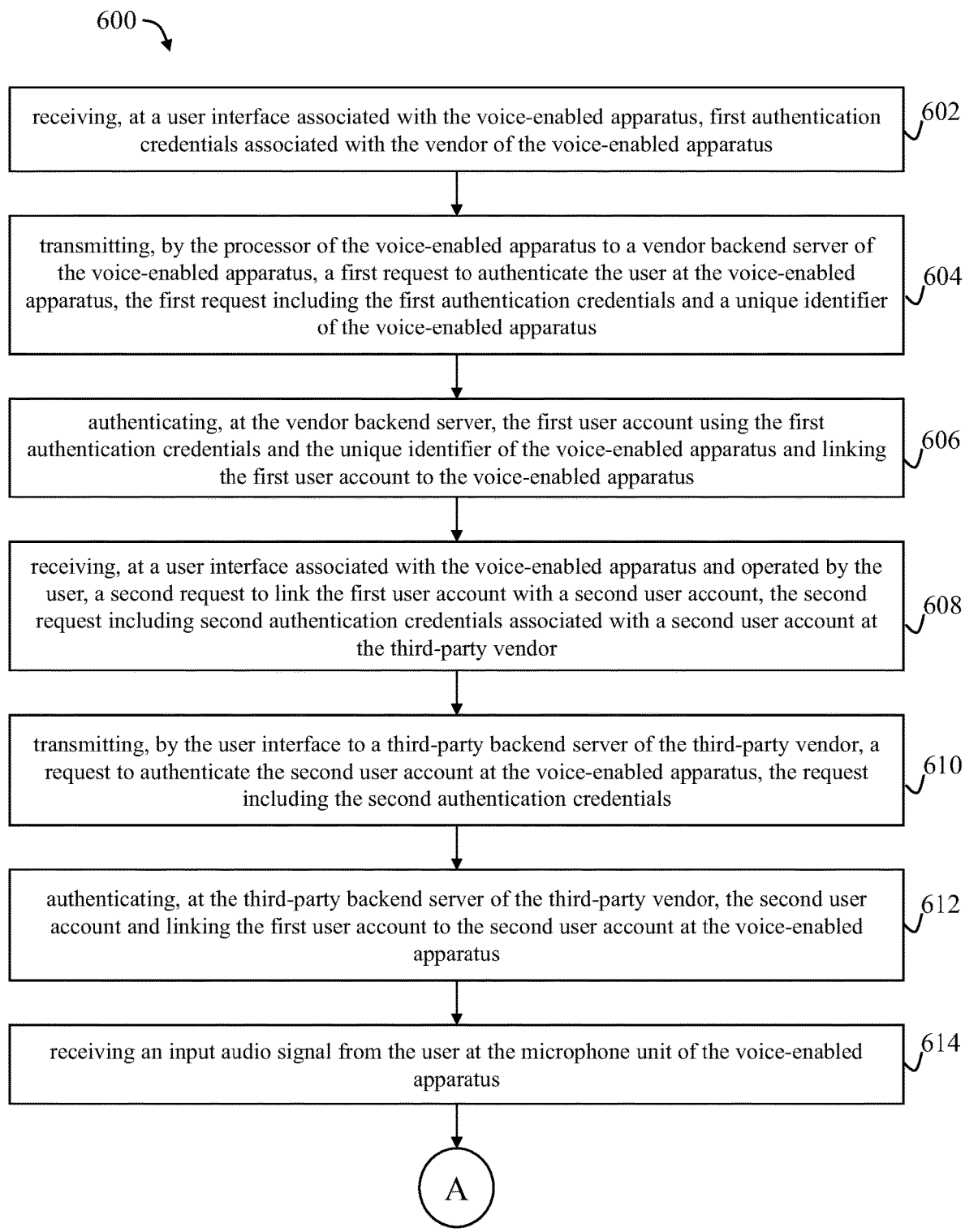
FIGS. 6A-B illustrate an exemplary flowchart illustrating a method for virtual assistant enhanced access of private information in accordance with an exemplary embodiment of the present disclosure.
Figure 6B:
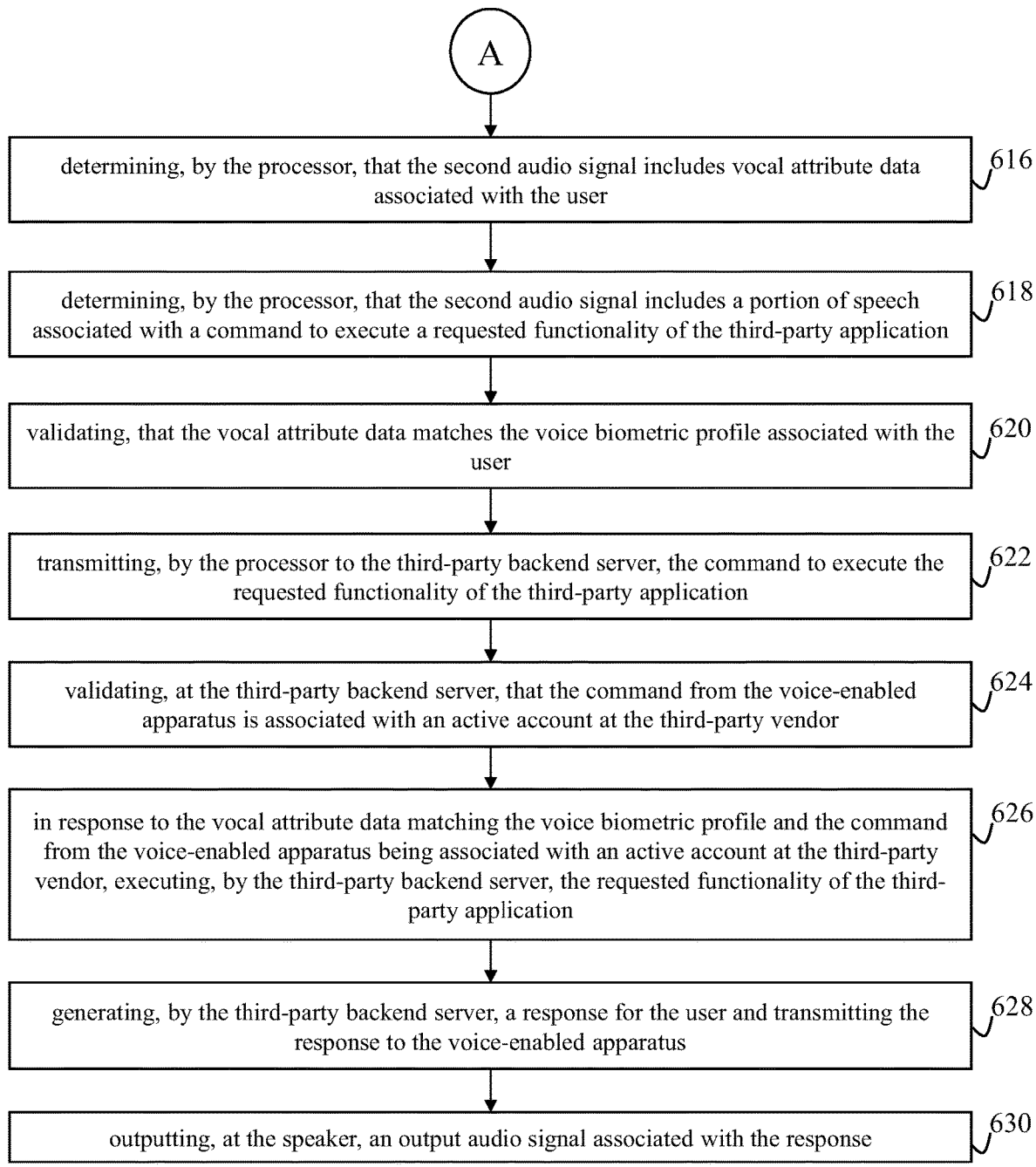

Referring to FIGS. 6A-6B, there is shown an exemplary diagram depicting a method of interacting with a voice-assisted member interface hosted by a provider backend server of a provider using a voice enabled-apparatus hosted by an apparatus vendor separate and distinct from the provider. The voice-enabled apparatus may include a microphone unit, a speaker and a processor coupled to the microphone unit and the speaker. The processor may be configured to cause the voice-enabled apparatus to perform one or more functions in response to audio signals received at the microphone unit.

In some embodiments, the method 600 may include the step 602 of receiving, at a user interface associated with the voice-enabled apparatus (e.g., virtual assistant 102), first authentication credentials associated with the vendor of the voice-enabled apparatus. For example, the virtual assistant 102 may receive user authentication credentials associated with a vendor specific account. In some embodiments, the method 600 may include the step 604 of transmitting, by the processor of the voice-enabled apparatus to a vendor backend server of the voice-enabled apparatus, a first request to authenticate the user at the voice-enabled apparatus, the first request including the first authentication credentials and a unique identifier of the voice-enabled apparatus. For example, the virtual assistant 102 may transmit, via the processor of the virtual assistant 102, the user authentication credentials associated with the user's vendor specific account and a PIN to the vendor server 104 for authentication with the vendor specific account.

In some embodiments, the method 600 may include the step 606 of authenticating, at the vendor backend server, the first user account using the first authentication credentials and the unique identifier of the voice-enabled apparatus and linking the first user account to the voice-enabled apparatus. For example, the vendor server 104 may receive the user authentication credentials and PIN and, in response to the authentication credentials and PIN being valid, associate the user's vendor specific account with the virtual assistant 102 (e.g., link the user's vendor specific account and the virtual assistant 102). In some embodiments, the method 600 may include the step 608 of receiving, at a user interface associated with the voice-enabled apparatus and operated by the user, a second request to link the first user account with a second user account, the second request including second authentication credentials associated with a second user account at the provider. For example, the user 110 may input, via the user interface shown in FIG. 2E displayed by virtual assistant 102, authentication credentials associated with the user's provider account.

In some embodiments, the method 600 includes the step 610 of transmitting, by the user interface to a provider backend server of the provider, a request to authenticate the second user account at the voice-enabled apparatus, the request including the second authentication credentials. For example, the user 110 may press the "login" button displayed on the user interface shown in FIG. 2E, causing the virtual assistant 102 to transmit the input authentication credentials to the provider server 106. In some embodiments, the method 600 includes the step 612 of authenticating, at the provider backend server of the provider, the second user account and linking the first user account to the second user account at the voice-enabled apparatus. For example, the provider server 106 may receive the user authentication credentials associated with the user's provider account and, in response to the authentication credentials being valid, authenticate the user's provider account and create an association between the provider account and the vendor specific account as discussed with reference to FIG. 4.

In some embodiments, the method 600 may include the step 614 of receiving an input audio signal from the user at the microphone unit of the voice-enabled apparatus. For example, a user 110 may provide a spoken command to the audio input 112 connected to virtual assistant 102. In some embodiments, the method 600 may include the step 616 of determining, by the processor, that the second audio signal includes vocal attribute data associated with the user. For example, the processor associated with virtual assistant 102 may process the spoken command from the user 110 to determine vocal attribute data which may be used for voice biometric authentication. In some embodiments, the method 600 may include the step 618 of determining, by the processor, that the second audio signal includes a portion of speech associated with a command to execute a requested functionality of the voice-assisted member interface. For example, the processor associated with the virtual assistant 102 may determine that the received spoken command included a command to execute a functionality of the voice-assisted member interface (e.g., requesting information related to healthcare benefits as discussed with reference to FIG. 5A).

In some embodiments, the method 600 may include the step 620 of validating, that the vocal attribute data matches the voice biometric profile associated with the user. For example, the virtual assistant 102 may determine, based on voice biometric data stored on the vendor server 104, that the vocal attributes included in the spoken command are valid (e.g., performing voice biometric authentication). In some embodiments, the method 600 may include the step 622 of transmitting, by the processor to the provider backend server, the command to execute the requested functionality of the voice-assisted member interface. For example, the processor associated with the virtual assistant 102 may transmit the request for healthcare benefit information, included in the spoken command from the user, to the provider server 106. In some embodiments, the method 600 may include the step 624 of validating, at the provider backend server, that the command from the voice-enabled apparatus is associated with an active account at the provider. For example, the provider server 106 may validate that the user's provider account includes an indication that the user 110 has a valid policy with the provider.

In some embodiments, the method 600 may include the step 626 of in response to the vocal attribute data matching the voice biometric profile and the command from the voice-enabled apparatus being associated with an active account at the provider, executing, by the provider backend server, the requested functionality of the voice-assisted member interface. For example, the provider server 106 may receive an indication that the voice biometric authentication succeeded and that the user 110 has a valid policy with the provider. The provider server 106 may perform the requested functionality, which in this example is to retrieve healthcare benefit information associated with the user's provider account. In some embodiments, the method 600 may include the step 628 of generating, by the provider backend server, a response for the user and transmitting the response to the voice-enabled apparatus. For example, the provider server 106 may generate a message indicating the requested healthcare benefit information associated with the user's provider account and transmitting the message to the virtual assistant 102. In some embodiments, the method 600 may include the step 630 of outputting, at the speaker, an output audio signal associated with the response. For example, the virtual assistant 102 may receive the generated response from the provider server 106 and output the response as an audio signal via audio output device 114.

In some embodiments, the method 600 may include that the output audio signal includes a prompt to the user to perform a subsequent user action. For example, the output audio signal may include an audible message asking the user 110 if they would like to perform another functionality of the voice-assisted member interface application and continue their current session as discussed above with reference to FIG. 5A. In some embodiments, the provider backend server stores protected health information corresponding to the user. For example, the provider server 106 may store protected health information associated with a user's provider account.

In some embodiments, the method 600 may include determining, by the processor, that no voice biometric data profile associated with the first user account exists, transmitting, by the processor, a request to the voice-enabled apparatus to display a request for the voice biometric data; and receiving and storing, at the vendor backend server, the voice biometric data profile. For example, the virtual assistant 102 may be configured to determine that no voice biometric data is stored on vendor server 104 that is associated with the user's vendor specific account. The virtual assistant 102 may prompt the user 110 to create a voice biometric data profile to be stored on the vendor server 104 as discussed with reference to FIGS. 3D-3F. In some embodiments, the user interface is at least one of: a graphical user interface and an audio user interface. For example, the virtual assistant 102 may be a smart speaker which includes an audio input and output device, the virtual assistant 102 may be a smart phone which includes a touch screen display, an audio input device, and an audio output device, or any other device as discussed above with reference to FIG. 1.

In some embodiments, the method 600 may include, before performing the step of linking the first user account to the second user account, determining, by the processor, that a voice biometric data profile associated with the user is stored on the vendor backend server. For example, the virtual assistant 102 may determine whether a voice biometric data profile associated with the user's vendor specific profile is stored on vendor server 104. In some embodiments, the method 600 may include in response to the voice biometric data profile not being stored on the vendor backend server conducting voice biometric training, at the voice enabled virtual assistant device, using audio signals from the user to generate the voice biometric data profile, and associating, by the vendor backend server, the generated voice biometric data profile with the first user account and storing the generated voice biometric data profile. For example, the virtual assistant 102 may determine that no voice biometric data profile associated with the user's vendor specific account is stored on vendor server 104 and may perform a voice biometric data profile setup as shown in FIGS. 3D-3F. In some embodiments, the method 600 may include in response to the voice biometric data profile being stored on the vendor backend server, proceeding to link the first user account to the second user account at the provider backend server. For example the association between the vendor specific account and provider account may not take place unless voice biometric data associated with the user's vendor specific profile is stored on the vendor server 104. In some embodiments, the voice-enabled apparatus (e.g., the virtual assistant 102) is HIPAA compliant.

Provider Search

In some embodiments, the virtual assistant 102 may be configured to return a list of healthcare providers based on a request from a user 110 to search for healthcare providers based on one or more criteria. For example, a user 110 may wish to find a list of healthcare practitioners that match specific criteria (e.g., gender, age, primary healthcare specialty, languages spoken), which the user 110 may provide to the virtual assistant 102. The healthcare provider search, as described herein, may be considered the invocation of a specific functionality of the voice-assisted member interface, and therefore, it will be understood that the authentication and validation as described above with reference to FIG. 5B may be required in order to perform the healthcare provider search. For sake of brevity, and so not as to obscure pertinent aspects of the present disclosure, it will be assumed that the voice biometric data and authorization token were each validated according to the method 550.

Figure 7:
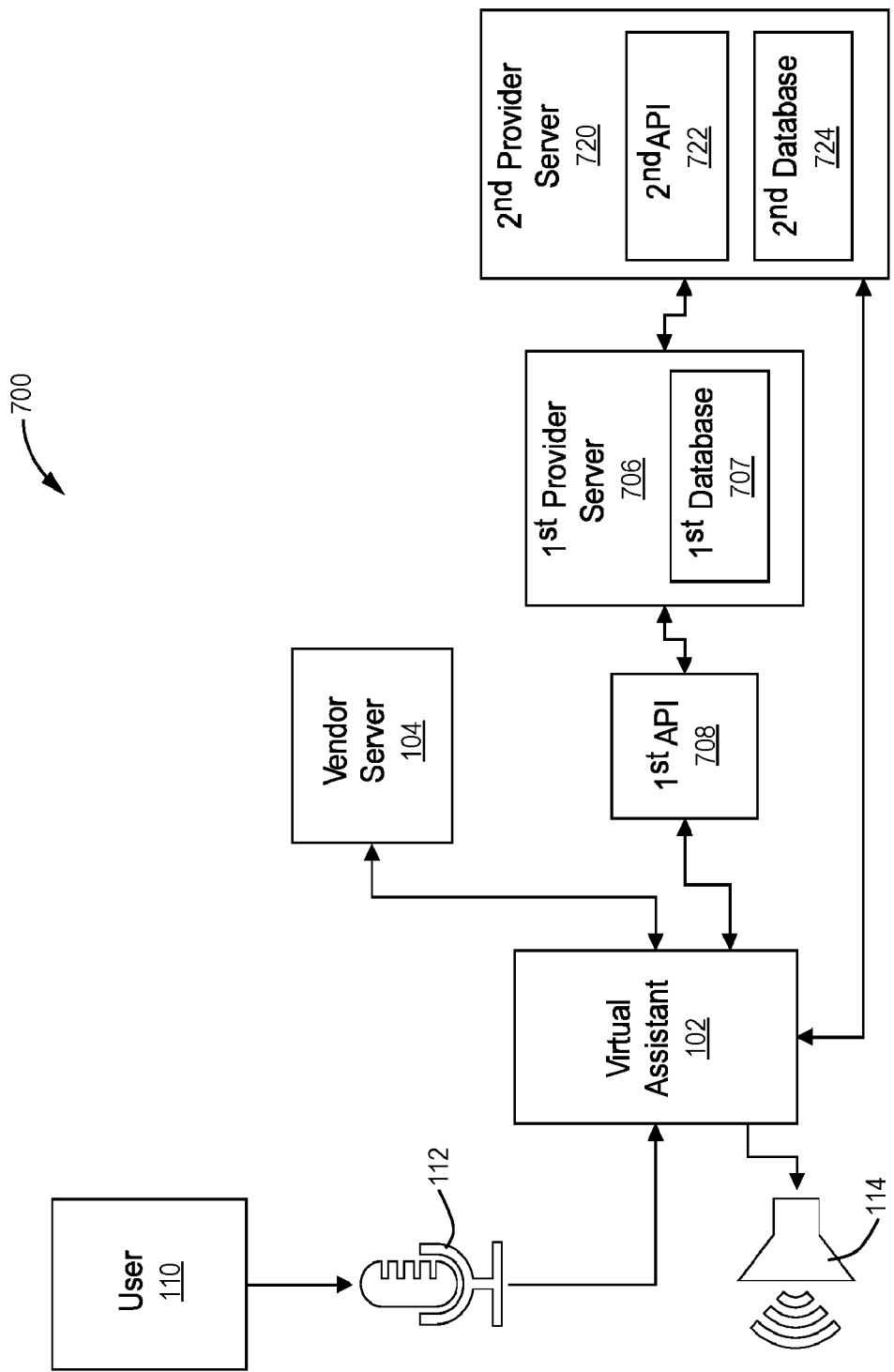
FIG. 7 is a block diagram illustrating an implementation of a system for virtual assistant enhanced access of information in accordance with an exemplary embodiment of the present disclosure.

Referring to FIG. 7, there is shown a block diagram illustrating an implementation of a system, generally designated 700, for virtual assistant enhanced access to information. While some example features are illustrated, various other features have not been illustrated for the sake of brevity and so as not to obscure pertinent aspects of the example embodiments disclosed herein.

The system 700 may be similar to the system 100, except that the provider server 106 is a first provider server 706 which is in communication with a second provider server 720. The first provider server 706 may be the same as provider server 106. The first provider server 706 may be associated with a health insurance provider. The system 700 may include the virtual assistant enabled device 102, the first provider server 706, the second provider server 720 and vendor server 104 in communication with the virtual assistant device 102.

In some embodiments, the user 110 may have an account that is associated with the second provider (e.g., a second provider specific account). The system 700 may be configured to access protected information (e.g., protected health or personal information) that is stored on the second provider server 720 to execute one or more functionalities requested by the user 110 at the virtual assistant 102. In some embodiments, the second provider server 720 may be configured to require one or more authentication means before any protected information pertaining to the user 110 is transmitted from the second provider server 720. The authentication means required by the second provider server 720 may be determined by the second provider and/or one or more protected information standards (e.g., HIPAA). The authorization token 410 may, in some instances, be used as the authentication means required by the second provider server 720. In some embodiments, using the authorization token 410 as an authentication means at the second provider server 720 includes adding one or more additional unique identifiers to the authorization token 410. For example, the authorization token 410, as described above, includes five unique identifiers. In order for the authorization token 410 to serve as an authentication means with the second provider server 720, one or more additional unique identifiers may be added such that there are more than five unique identifiers included in the authorization token 410. The exact unique identifiers may be determined by the first and/or second providers. For example, the one or more additional unique identifiers may include the user's second provider specific username, and a unique randomly generated identifier that is created by the second provider server 720. In other embodiments, the authentication means established between the first and second provider servers 706, 720 does not include the use of the authorization token 410. For example, the authentication means between the first provider server 706 and second provider server 720 may include the use of an authorization token that is separate and distinct from the authorization token 410. It will be understood though, however, that authentication means between the first and second provider servers 720 may be required to be established in order for protected information to be transmitted from the second provider server 720 to the first provider server 706 and/or the virtual assistant 102. In this manner, a functionality of the voice-assisted member interface which requires protected information from the second provider server 720 may require that the user's identity be authenticated at the second provider server 720.

The data stored on the second provider server 720 and/or second database 724, which functionalities of the voice-assisted member interface may require, may be, for example, data stored in an electronic medical record (EMR) system. EMR systems may include, for example, a listing of providers, calendars and/or protected information relating to the user 110.

The system 700 may be configured to receive a voice command from a user 110 which includes a request to conduct a search for a healthcare provider and/or practitioner, generally referred to as a healthcare provider search, based on one or more criteria (e.g., gender, preferred language, healthcare specialty, location). The virtual assistant 102 may return, to the user 110, a list of healthcare practitioners which match the search criteria provided by the user 110. A healthcare practitioner may refer to, as a non-limiting example, a doctor of medicine or osteopathy, a podiatrist, a dentist, a chiropractor, clinical psychologist, optometrist, nurse practitioner, nurse-midwife, and/or a clinical social worker.

The second provider server 720 may be a server associated with a healthcare provider or organization such as, for example, a hospital, doctors office, or a clinic, having stored thereon healthcare practitioner data required to perform the healthcare provider search. The data stored on the second provider server 720 may include data relating to healthcare practitioners (e.g., a doctor of medicine or osteopathy, podiatrist, dentist, chiropractor, clinical psychologist, optometrist, nurse practitioner, nurse-midwife, or a clinical social worker) associated with the healthcare provider. For example, the second provider server 720 may store data related to different healthcare practitioner's names, ages, genders, languages (e.g., English, Spanish), work locations, healthcare specialties, and/or years of experience.

In the embodiment shown in FIG. 7, a single second provider server 720 is illustrated as being in communication with first provider server 706. However, it will be understood that there may be a plurality of second provider servers associated with different healthcare providers in communication with first provider server 706. The second provider server 720 may be a plurality of servers each associated with a different healthcare provider and each having stored thereon healthcare practitioner data. It will be understood in the following disclosure and examples that the second provider server 720 may be one or more servers having stored thereon healthcare practitioner data required to execute a healthcare provider search. For example, if a requested healthcare provider search would require that two datasets stored on different servers be queried in order to execute the healthcare provider search, then second provider server 720 includes the said two servers.

The virtual assistant 102 may have installed thereon the voice-assisted member interface, as discussed with reference to FIG. 1, which may include executable code configured to perform the functionality discussed herein.

The virtual assistant 102 may be configured to receive, via the audio input device 112, a spoken command from the user 110 which includes a request to perform a healthcare provider search. The spoken command may include one or more search criteria which the user 110 wishes to include in the health provider search.

The virtual assistant 102 may be configured to convert the spoken command into a computer readable text and transmit the computer readable text to the first provider server 706. The computer readable text may include an indication of the requested functionality (e.g., a request for a provider search) as well one or more search criteria. For example, a user 110 may speak a command such as "find a female OB/GYN who speaks Spanish in my area" and the virtual assistant 102 may convert the spoken command into a series of search criteria such as the gender being equal to female, the healthcare specialty being equal to OB/GYN, that a language spoken by said healthcare practitioner include Spanish, and that the place of work for the healthcare practitioner be within a certain distance of the user's 110 zip code or place of residence. In some embodiments, the virtual assistant 102 may be configured to convert the spoken command to search criteria including, but not limited to: location (e.g., city, state, zip code), date of birth, name, title (e.g., OB/GYN), healthcare network, spoken languages, hours of availability, primary healthcare specialty, secondary healthcare specialty, and taxonomy.

The virtual assistant 102 may transmit the search request, with the converted search criteria, to the first provider server 706 in order to execute the requested search. In some embodiments, service oriented architecture (SOA) and/or an application programming interface (API) is used by the voice-assisted member interface to cause the virtual assistant 102 to request and receive the healthcare provider search results from the first provider server 706.

In some embodiments, the first provider server 706 is configured to determine, based on the received computer readable text corresponding to the spoken command, if a provider search is being requested. For example, a user 110 may provide a spoken command of "what is a deductible" which is converted to computer readable text, via the virtual assistant 102, and transmitted to the first provider server 706. The first provider server 706 may determine, based on the converted text, that no provider search is being requested. Alternatively, the user 110 may provide a spoken command of "providers who speak Spanish near me" which is converted to computer readable text, via the virtual assistant 102, and transmitted to the first provider server 706. The first provider server 706 may determine, based on the converted text, that a provider search is being requested.

In response to determining that a provider search is being requested, the first provider server 706 may be configured to determine whether a second API 722 is associated with the second provider server 720. If a second API 722 is associated with the second provider server 720, the first provider server 706 may transmit the search criteria to the second provider server 720 to cause the second API 722 to execute the provider search based on the received search criteria. For example, the first provider server 706 may transmit the provider search request including search criteria corresponding to a female OB/GYN doctor within five miles of the user 110 to the second provider server 720. The second API 722 may be configured to cause the second provider server 720 to query a database (e.g., second database 724) associated with the second provider server 720 based on the search criteria. The second database 724 may have stored thereon data relating to one or more healthcare practitioners associated with the second provider, such as the healthcare practitioners name, age, gender, primary healthcare specialty, working hours, working location, spoken/understood languages, and/or taxonomy. The second API 722 may be configured to cause the second provider server 720 to query second database 724, based on the search criteria received from the first provider server 706, and generate a resulting list of search results. The list of search results may be in a computer readable format such as a .xlsx, or .txt format. For example, the second provider server 720 may generate, via second API 722, a computer readable list (e.g., .xlsx, .txt) which includes the name, age, gender, primary and secondary healthcare specialties, available hours, contact information, languages spoken, and place of business of all healthcare practitioners which match the search criteria.

In response to generating the list of search results, the second API 722 may transmit the list of search results to the first provider server 706. The first provider server 706, in response to receiving the generated list of search results, may transmit the list of search results to the virtual assistant 102. In response to receiving the list of search results, the virtual assistant 102, via the voice-assisted member interface and first API 707, may be configured to output to the user 110 the search results. In some embodiments, the voice-assisted member interface may be configured to process the received list of search results and cause the virtual assistant 102, via the first API 707, to output the list of search results via one or more output devices to the user 110. The one or more output devices may include an audio output device 114, and/or a visual display device (not shown) in communication with the virtual assistant 102. In some embodiments, the voice-assisted member interface may be configured to transmit the search results to the user 110 via electronic mail.

In some instances, in response to determining that a provider search is being requested, the first provider server 706 may determine that no second API 722 is associated with the second provider server 720. For example, as mentioned above, the second provider server 720 may be any number of servers associated with different healthcare providers. At least one of said servers may not include an associated API (e.g., no second API 722). In response to determining that no second API 722 is associated with the second provider server 720, the first provider server 706 may be configured to transmit a request to the second provider server 720 including a request for data stored on the second database 724 associated with the second provider server 720.

In response to receiving the request for data stored on second database 724, the second provider server 720 may be configured to transmit healthcare practitioner data, stored on a second database 724, to a first database 707 associated with the first provider server 706. In response to receiving the healthcare practitioner data, the first provider server 706 may be configured to query database 707 based on the converted search criteria received from the virtual assistant. For example, first provider server 706 may execute a search, on the healthcare practitioner data, received from second database 724 and stored on first database 707, for healthcare practitioners within a certain range of a user's address that also speak Spanish. The first provider server 706 may be configured to generate a list of search results, based on the results of the query of database 707. For example, the first provider server 706 may generate a computer readable list (e.g., .xlsx, .txt) which includes the name, age, gender, primary and secondary healthcare specialties, available hours, contact information, languages spoken, and place of business of all healthcare practitioners which match the search criteria.

The first provider server 706, in response to generating list of search results, may transmit the list of search results to the virtual assistant 102. In response to receiving the list of search results, the virtual assistant 102, via the voice-assisted member interface and first API 707, may be configured to output to the user 110 the search results. In some embodiments, the voice-assisted member interface may be configured to process the received list of search results and cause the virtual assistant 102, via the first API 707, to output the list of search results via one or more output devices to the user 110. The one or more output devices may include an audio output device 114, and/or a visual display device (not shown) in communication with the virtual assistant 102. In some embodiments, the voice-assisted member interface may be configured to transmit the search results to the user 110 via electronic mail. In some embodiments, the virtual assistant 102 may be configured to not return the list of healthcare providers until the user 110 has completed the voice biometric setup and/or account association method, as shown in, for example, FIGS. 2A-4. In other embodiments, the virtual assistant 102 may be configured to return the list of healthcare providers regardless of whether the user 110 has completed the voice biometric setup and/or the account association method, as shown in, for example, FIGS. 2A-4.

Figure 8:
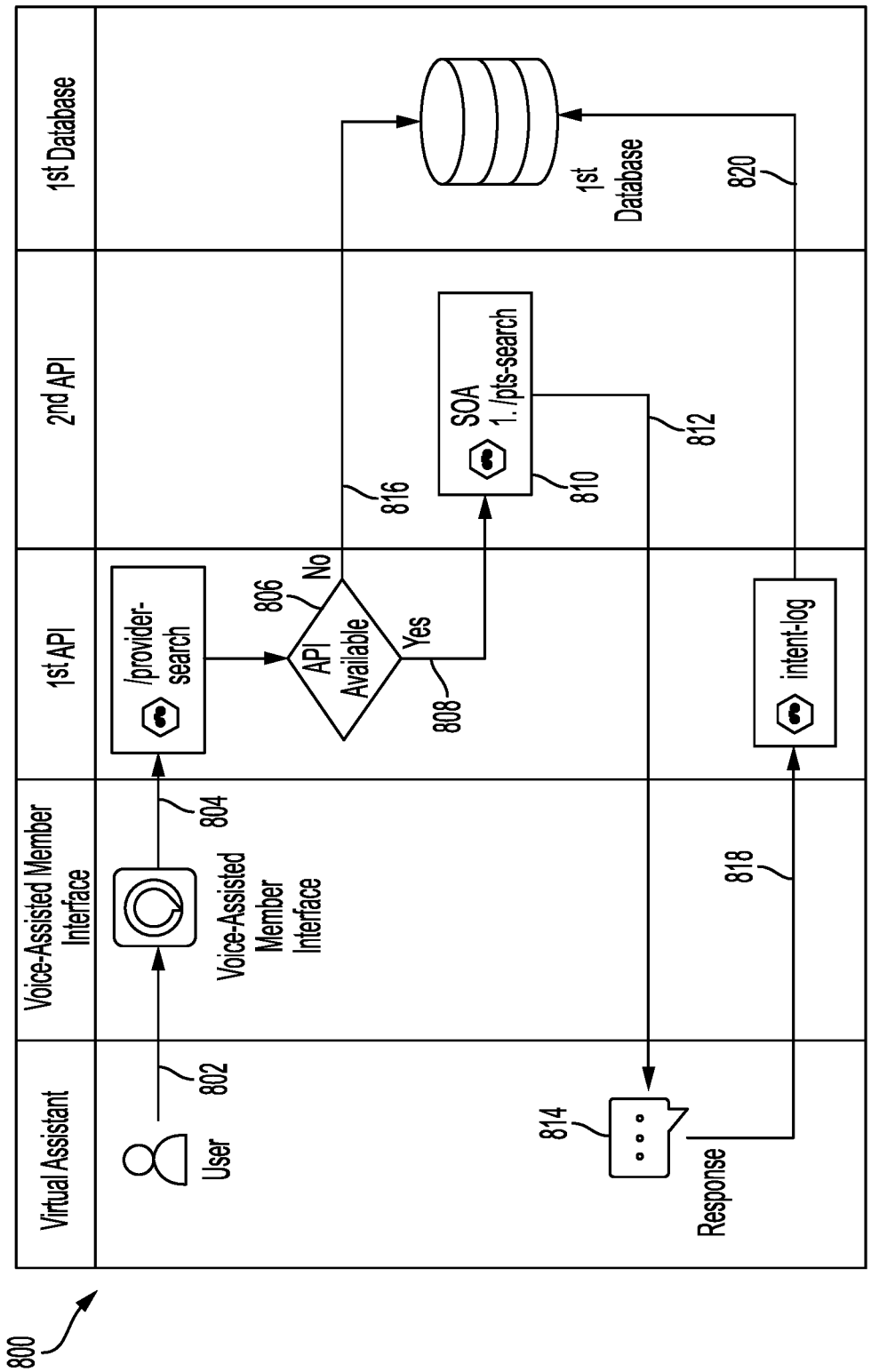
FIG. 8 illustrates an exemplary diagram depicting a method of conducting a service provider search in accordance with an embodiment of the present disclosure.

Referring to FIG. 8, there is shown an exemplary diagram depicting a method of conducting a healthcare provider search via a voice enabled virtual assistant device in accordance with an exemplary embodiment of the present disclosure. In some embodiments, prior to the method 800 the virtual assistant 102 may receive a spoken command from a user 110 and convert the spoken command to computer readable text. The spoken command may include an indication that a health provider search is being requested and may include one or more search criteria to be used in the health provider search.

In some embodiments, the method 800 may include step 802 of transmitting the computer readable text, corresponding to the converted spoken command, to a voice-assisted member interface installed on the virtual assistant 102. The voice-assisted member interface may be configured to process the computer readable text to determine if a health provider search is being requested.

In some embodiments, the method 800 includes the step 804 of, in response to determining that a health provider search is being requested, transmitting a request to execute computer executable code associated with the voice-assisted member interface, via the first API 708 associated with the first provider server 706, the computer executable code configured to initiate the health provider search.

In some embodiments, the method 800 includes the step 806 of determining if an API (e.g., second API 722) is associated with the second provider server 720.

In some embodiments, in response to a second API 722 being associated with the second provider server 720, the method 800 includes the step 808 of transmitting to the second API 722, from the first provider server 706, the one or more search criteria included in the computer readable text.

The method 800 may include the step 810 of querying a database associated with the second provider server 720 (e.g., second database 724) based on the one or more search criteria. In some embodiments, the second API 722 is configured to query the second database 724 based on the one or more search criteria. In some embodiments, the second API 722, in response to querying the second database 724, is configured to generate a list of search results including a listing of healthcare practitioners which match the one or more search criteria.

In some embodiments, the method 800 includes the step 812 of transmitting the generated list of search results to the virtual assistant 102, via the second API 722. In some embodiments, the generated list of search results is transmitted to the first provider server 706 and the first provider server 706 transmits the generated list of search results to the virtual assistant 102.

In some embodiments, the method 800 includes the step 814 of outputting the generated list of search results, via the virtual assistant 102, to the user 110. In some embodiments, the output may be one or more of an output on a visual display, an audio output, and/or sending an electronic message to the user 110. For example, the virtual assistant 102 may be in communication with a visual display device and may generate a graphical display on the visual display device, based on the list of search results, which displays to the user the healthcare practitioners included in the list of search results. The virtual assistant 102 may also be in communication with an audio output device (e.g., a speaker) which is configured to generate an audible output. The virtual assistant 102 may generate a signal, based on the list of search results, and transmit the signal to the audio output device, causing the audio output device to output an audible sound corresponding to the list of search results. For example, the audio output device may output a sound which includes a listing of the healthcare practitioners included in the list of search results.

Returning to step 806, in response to determining that no API is associated with the second provider server 720, the method may include the step 816 of querying a database (e.g., first database 707) associated with the first provider server 706, via the first API 708, based on the one or more search criteria. In some embodiments, the first database 707 may have previously received data stored on second database 724 corresponding to healthcare practitioners associated with the second provider server 720. In some embodiments, the first provider server 706, via the first API 708, may generate a list of search results based on the query of the first database 707 and transmit the generated list of search results to the virtual assistant 102.

In some embodiments, the method 800 may proceed to step 814 of outputting the generated list of search results to the user 110 via the virtual assistant 102, as discussed above.

In some embodiments, the method 800 may include the step 818 of transmitting, from the virtual assistant 102 to the first provider server 706 a record of the spoken command from step 802 and/or the response generated in step 814. In some embodiments, the generated response includes the generated list of healthcare practitioners which match the one or more search criteria. In some embodiments, the method 800 may include the step 820 of transmitting from the first provider server 706, via the first API 708, to the first database 707, the record of the spoken command and/or generated response. In some embodiments, the first database 707 may store the record of the spoken command and/or generated response for retrieval at a later point in time.

Figure 9:
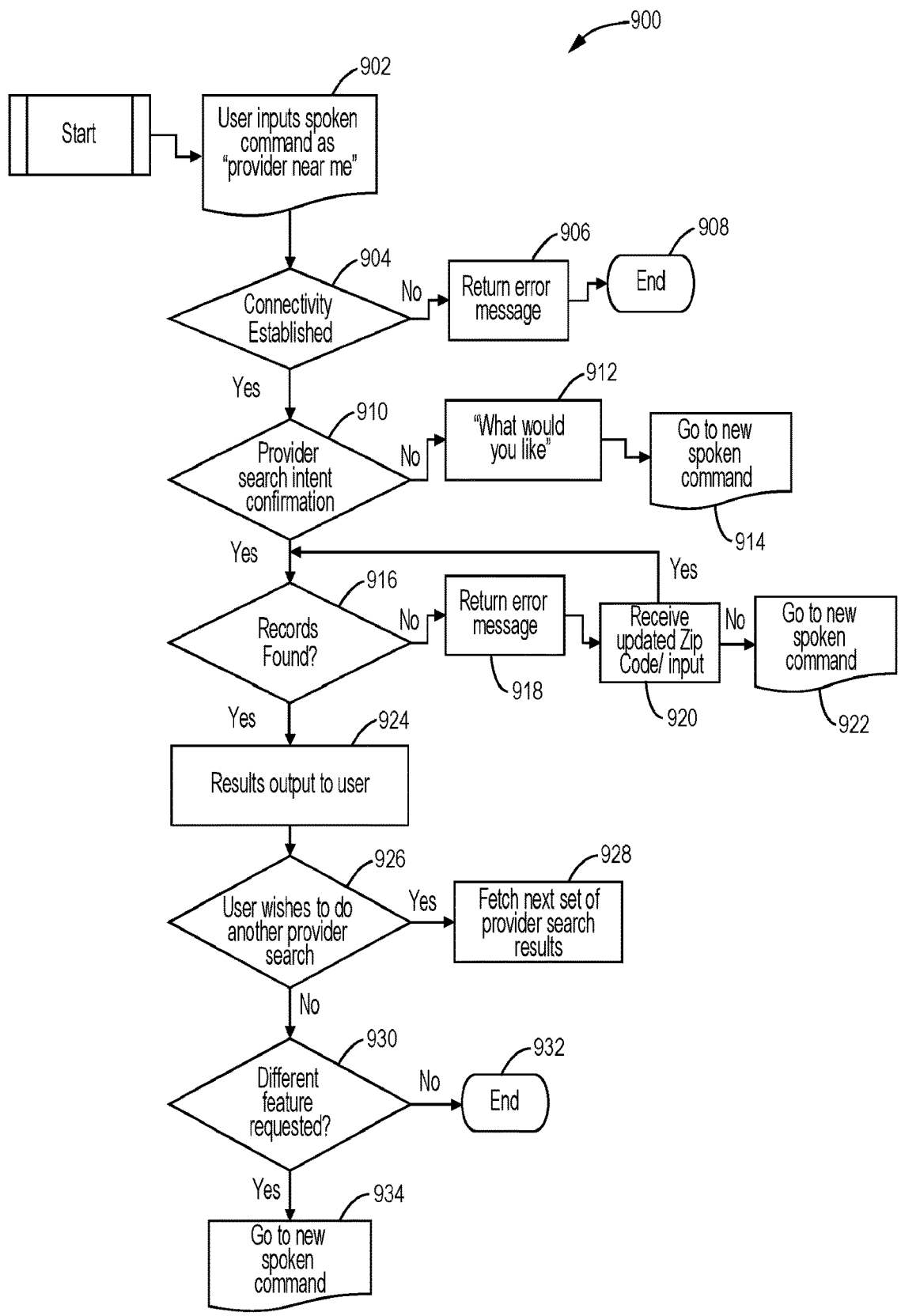
FIG. 9 illustrates an exemplary diagram depicting a method of conducting a service provider search in accordance with another embodiment of the present disclosure.
Figure 10A:
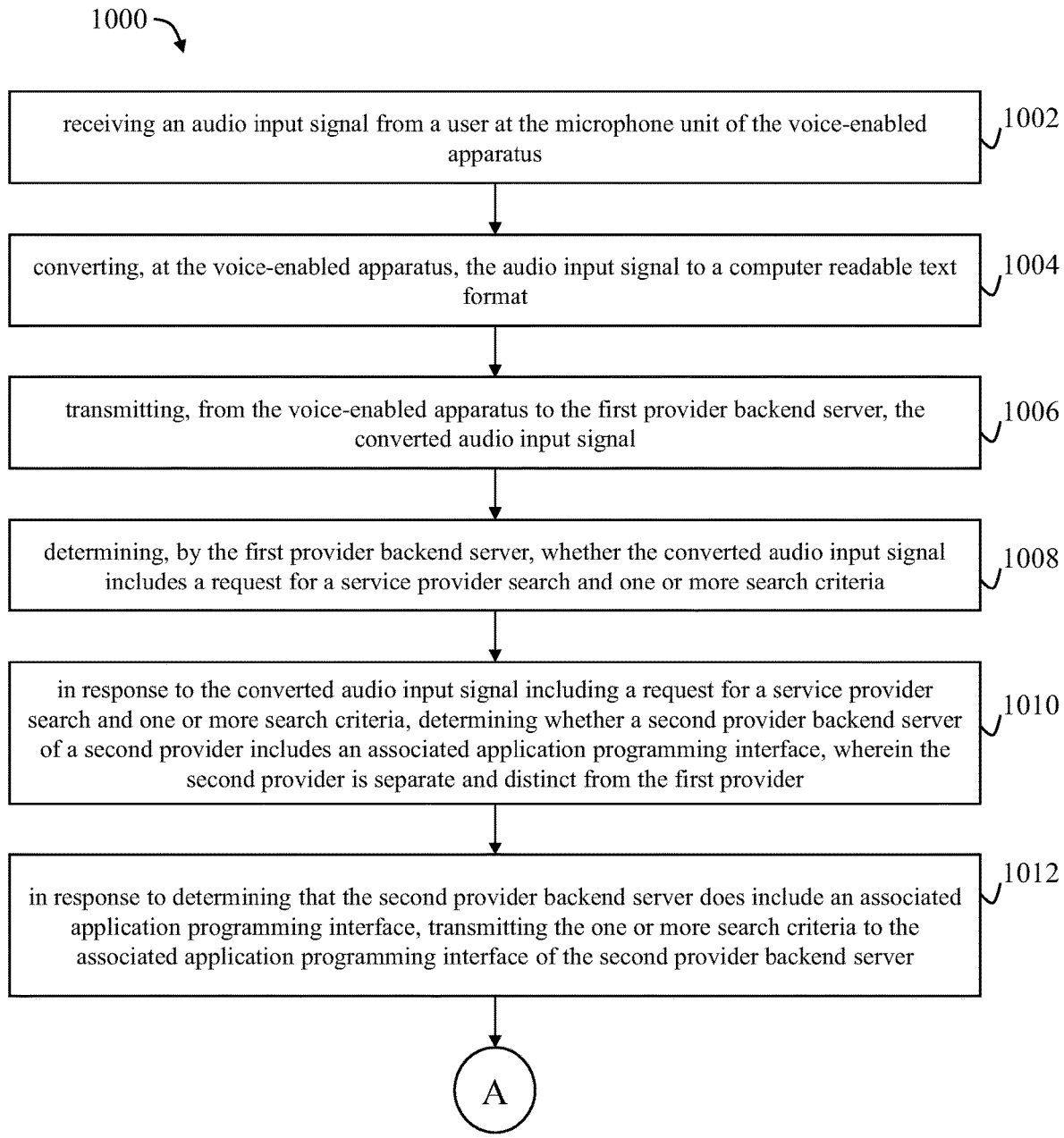
FIGS. 10A-10B illustrate an exemplary flowchart illustrating a method for virtual assistant enhanced access to service provider search information in accordance with an exemplary embodiment of the present disclosure.
Figure 10B:
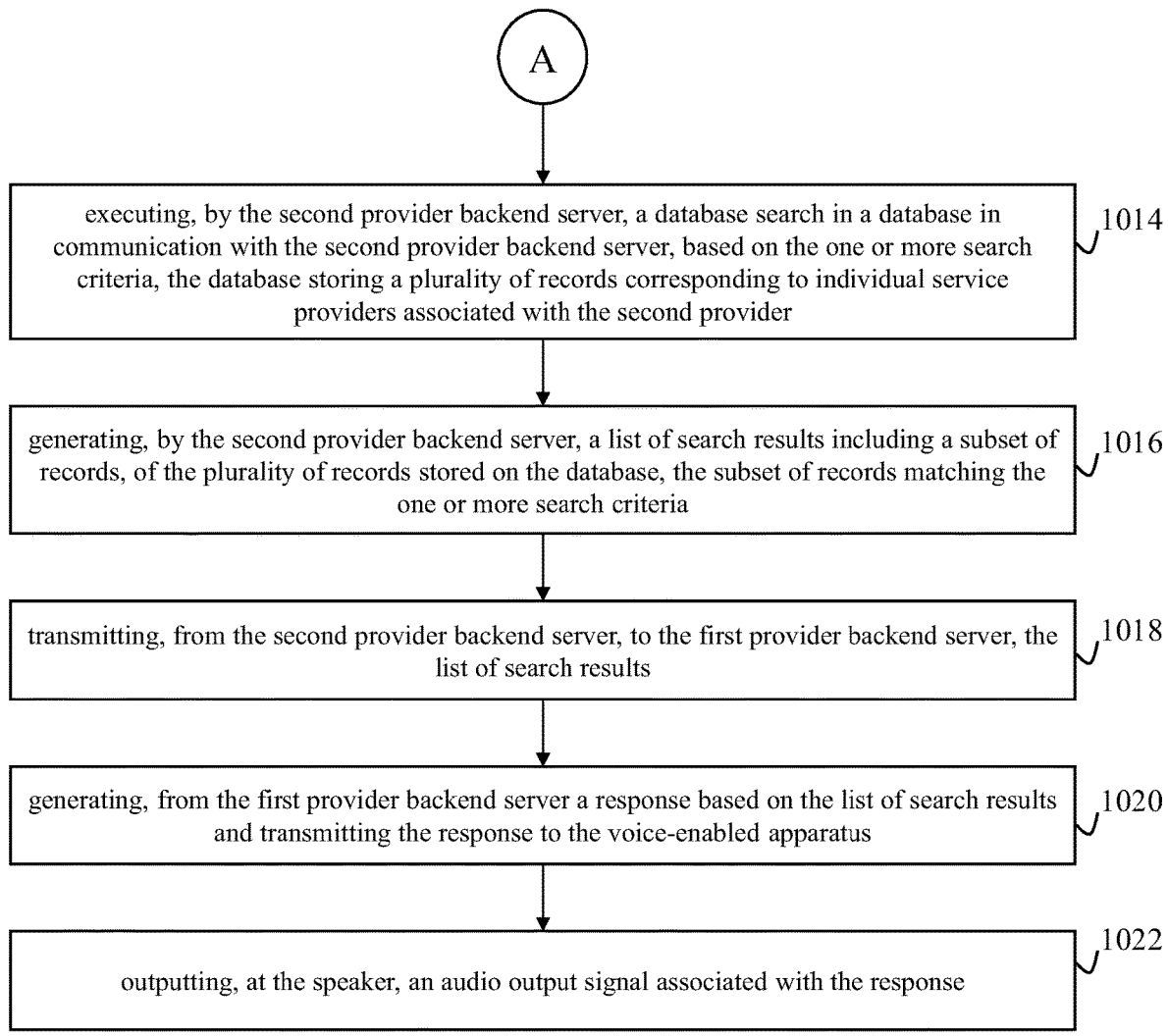

Referring to FIG. 9, there is shown an exemplary diagram depicting a method of conducting a healthcare provider search via a voice enabled virtual assistant device in accordance with an exemplary embodiment of the present disclosure. In some embodiments, the method 900 may include the step 902 of a user (e.g., user 110) providing an input as a spoken command. In the example shown in FIG. 9, the spoken command is "provider near me" which corresponds to a request to perform a healthcare provider search for healthcare providers near the user 110. In some embodiments, the user 110 provides the spoken command input to a virtual assistant enabled device (e.g., virtual assistant 102) configured to receive inputs as spoken commands. In some embodiments, the method 900 may include the step 904 of establishing connectivity to one or more networks and/or servers (e.g., first provider server 706, second provider server 720). In some embodiments, the virtual assistant 102 may be a network enabled device configured to perform step 904. In some embodiments, if no connectivity is established, the method 900 may include the step 906 of outputting an error message to the user 110, via virtual assistant 102. In response to the error message being displayed to the user 110, the method 900 may terminate at step 908.

In some embodiments, if connectivity is established, the method 900 may include the step 910 of confirming that a provider search was requested by user 110. For example, the virtual assistant 102 may be configured to convert the spoken command into computer readable text which the voice-assisted member interface is configured to process to determine if the spoken command includes a provider search request. In some instances, if the spoken command does not include a provider search request, the method 900 may include the step 912 of outputting to the user 110 a prompt requesting a new spoken command (e.g., output of "what would you like?"). In some embodiments, the user 110 may provide a new spoken command such as a provider search request, or a request for a different functionality (e.g., healthcare term lookup). In response to the new spoken command, the method 900 may include the step 914 of executing the new spoken command.

Returning to step 910, in some instances, the virtual assistant 102, via the first API 708 and/or the voice-assisted user interface, may determine that a provider search request was included in the spoken command. In some embodiments, in response to a provider search request being confirmed the method 900 may include the step 916 of querying the first database 707 and/or the second database 724 to determine if any records match the search criteria included in the spoken command. For example, step 916 may be similar to steps 806 through 810 and/or steps 806 and 816 in method 400 depending on whether a second API 722 is associated with a second provider server 720. In some instances, no records matching the search criteria included in the spoken command may be found. In some embodiments, if no records are found, the method 900 may include the step 918 of outputting an error message to the user 110, via the virtual assistant 102, indicating that no records were found. In some embodiments, the method 900 may include the step 920 of requesting updated search criteria (e.g., an updated zip code), via the virtual assistant 102. For example, the user 110 may provide a spoken command to broaden the search criteria (e.g., "providers who are an OB/GYN"). If no updated search criteria is received, the method 900 may include the step 922 of proceeding to a new spoken command. In other embodiments, if no updated search criteria is received the method 900 may terminate. If new search criteria is received, at the virtual assistant 102, the method 900 may return to step 916 to determine if records corresponding to the new search criteria are found.

Returning to step 916, in some instances records may be found which correspond to the search criteria (e.g., original or new). If records are found which correspond to the received search criteria, the method 900 may include the step 924 of outputting, to the user 110, via virtual assistant 102 the results of the provider search (e.g., the records that were found). Step 924 may be the same or similar to step 814 as discussed with reference to method 800 and will not be discussed again for sake of brevity. In some embodiments, the method 900 may include the step 926 of determining whether the user 110 has input a new provider search request at virtual assistant 102. In some instances the user 110 does input a new provider search request at the virtual assistant 102 and the method 900 may include the step 928 of performing a query, based on the search criteria provided in the new provider search request. Step 928 may include repeating step 916 to determine if records are found corresponding to the new provider search request. In some instances, the user 110 does not input a new provider search request. In some embodiments, if no new provider search request is input by the user 110, the method 900 may include the step 930 of determining if a different feature has been requested by the user 110. The feature may be requested via a spoken command from the user 110 at virtual assistant 102. A feature may refer to a collection of executable code, included in the voice-assisted member interface, configured to cause the virtual assistant 102 to perform a specific task. The voice-assisted member interface may have a plurality of different features corresponding to different tasks. For example, the provider search request discussed herein is a feature of the voice-enabled member interface. Other features may include scheduling appointments, providing definitions and/or explanations of medical and/or healthcare related terms, and/or providing a listing of symptoms for medical issues (e.g., the flu, COVID-19, a hernia, kidney stones), which are discussed below in more detail. In some embodiments, if no feature is requested, the method 900 may terminate at step 932. In some embodiments, if a feature is requested, the method 900 may include step 934 of executing the requested feature included in a spoken command from the user 110.

Further Features/Functionalities

The voice-enabled virtual assistant may be configured to execute a plurality of functionalities, as discussed above with reference to FIG. 5B, corresponding to spoken commands input by the user 110 at virtual assistant 102 other than the provider search feature. For each of the functionalities described herein, it will be assumed that voice biometric data and the authorization token, as discussed above with reference to FIG. 5B, were validated according to the method 550. Referring to FIG. 7, in some embodiments, the voice-assisted member interface may be configured to provide a listing of symptoms for a plurality of medical conditions, in response to a spoken command from the user 110 at virtual assistant 102. For example, the user 110 may input a spoken command, at virtual assistant 102, asking "What are the symptoms of COVID-19?". The virtual assistant 102, via the voice-enabled member interface, may be configured to transmit a request to the first provider server 706 requesting data including the symptoms of the medical condition included in the spoken command (e.g., COVID-19). In some embodiments, the first database 707, associated with the first provider server 706, may have stored thereon, data including lists of symptoms for a plurality of medical conditions. In other embodiments, the first provider server 706 is in communication with one or more external databases and/or servers (not shown) which includes the lists of symptoms for the plurality of medical conditions. The first provider server 706 may be configured to query one or more of first database 707 and an external database and/or server based on the spoken command. For example, the user 110 requested a list of symptoms for COVID-19, and the first provider server 706 may query first database 707 and/or an external database/server to retrieve a list of symptoms for COVID-19. In some embodiments, the first provider server 706 may generate a list of symptoms for the requested medical condition and transmit the list of symptoms to the virtual assistant 102. The virtual assistant 102 may be configured to output the list of symptoms to the user 110 via one or more of audio output, graphical display, and/or electronic message similar to the methods of output for the provider search request discussed above.

In some embodiments, the voice-assisted member interface may be configured to provide the severity of a medical condition in response to a spoken command input by a user 110 at virtual assistant 102. For example, the user 110 may input a spoken command of "What is the severity of kidney stones?" at virtual assistant 102. The virtual assistant 102 may be configured to convert the spoken command into computer readable text. The virtual assistant 102, via the voice-enabled member interface and/or the first API 708, may transmit a request for severity information corresponding to the medical condition (e.g., kidney stones) to the first provider server 706 including the converted computer readable text corresponding to the spoken command. The first provider server 706, in response to receiving the request, may be configured to query first database 707 and/or an external database/server having stored thereon severity information for the requested medical condition (e.g., kidney stones) and generate severity information relating to the medical condition. The severity information may be a text file, or any other computer readable format, which includes an explanation as to the severity of the medical condition. The first provider server 706 may be configured to transmit the severity information to the virtual assistant 102. In response to receiving the severity information, the virtual assistant 102 may be configured to output the severity information to the user 100 via one or more of audio output, graphical display, and/or electronic message similar to the methods of output for the provider search request discussed above.

In some embodiments, the voice-assisted member interface may be configured to provide a definition and/or explanation of a medical and/or healthcare related term in response to a spoken command input by user 110 at virtual assistant 102. For example, a user 110 may input a spoken command "What is a PCP" at the virtual assistant 102. The virtual assistant 102 may be configured to convert the spoken command into computer readable text. The virtual assistant 102, via the voice-enabled member interface and/or the first API 708, may transmit a request for medical and/or healthcare terminology definitions (e.g., a "PCP") to the first provider server 706 including the converted computer readable text corresponding to the spoken command. The first provider server 706, in response to receiving the request, may be configured to query first database 707 and/or an external database/server having stored thereon medical terminology definitions for the requested medical term (e.g., "PCP") and generate terminology information including the definition of the medical and/or healthcare related term. In this example, the requested medical term is "PCP" and the corresponding terminology information may include that "PCP is a primary care physician". The terminology information may be a text file, or any other computer readable format, which includes a definition of the requested healthcare and/or medical term. The first provider server 706 may be configured to transmit the terminology information to the virtual assistant 102. In response to receiving the terminology information, the virtual assistant 102 may be configured to output the terminology information to the user 100 via one or more of audio output, graphical display, and/or electronic message similar to the methods of output for the provider search request discussed above.

In some embodiments, the voice-assisted member interface may be configured to provide an appointment scheduling feature which allows the user 110 to schedule an appointment with a healthcare provider/practitioner, in response to a spoken command from the user 110 received at virtual assistant 102. For example, a user may input a spoken command "Schedule an appointment during the first week of April preferably in the morning" at the virtual assistant 102. In this example, the spoken command includes an indication as to the specific timeframe (e.g., first week of April) when the user 110 wishes to schedule an appointment. In some embodiments, the spoken command may include a wish to schedule the appointment with a specific healthcare practitioner. The specific healthcare practitioner may be previously associated with the user 110 and/or identified in a preceding provider search. For example, referring to method 900, in step 916 and 924 records including a listing of healthcare practitioners are identified and output to the user 110. The user 110 may then, at step 930 input a spoken command to schedule an appointment with one of the healthcare practitioners displayed to the user at step 924.

The virtual assistant 102 may be configured to convert the spoken command (e.g., the request to schedule an appointment) into computer readable text and transmit the computer readable text to the first provider server 706. The first provider server 706, in response to receiving the request, may be configured to identify a second provider server 720 associated with the healthcare practitioner for whom the user 110 wishes to schedule an appointment with. In this example, the healthcare practitioner is Doctor Smith who works at a clinic having an associated provider server. In response to identifying the corresponding second provider server 720, the first provider server 706 may transmit a request for a scheduling means to the second provider server 720. The second provider server 720, in response to receiving the request from the first provider server 706, may transmit the scheduling means to the first provider server 706. The scheduling means may be a hypertext transfer protocol address (e.g., a web address) corresponding to a website where users may schedule appointments with the desired healthcare practitioner. In response to receiving the scheduling means, the first provider server 706 may be configured to transmit the scheduling means (e.g., the web address) to the user 110 via electronic mail. This may allow the user 110 to access the healthcare providers preferred scheduling means in order to schedule an appointment with their desired healthcare practitioner.

In some embodiments, if the user's vendor specific account is associated with the second provider specific account, the voice-assisted member interface may allow the user to establish a dialogue with the virtual assistant 102 in order to schedule the appointment with the healthcare practitioner/provider via solely spoken commands. For example, in response to the above spoken command of "Schedule an appointment for the first Week of April, preferably in the morning", the voice-assisted member interface may cause the virtual assistant 102 to communicate with the second provider server 720, database 724 and/or an EMR used by the second provider to view the scheduling availability for the desired time frame (e.g., first week of April, preferably in the morning). The virtual assistant 1023 may receive said scheduling information and determine what availabilities fall within the desired time frame. In response to determining available appointment times within the desired time frame, if there are any, the virtual assistant 102 may output via the audio output device, the information relating to available appointment times to the user 110. For example, the output information may include "There is a 7:00 AM appointment available on April $1^{st}$, an 8:30 AM appointment available on April $3^{rd}$, and a 6:00 AM appointment available on April $5^{th}$, do any of these work for you?".

As such, the output information may include an indication that further input is required from the user 110. For example, the user 110 in this example is presented with three appointment options and is asked if any of them are suitable. The user 110 may provide a second spoken command input indicating which appointment they would like to select, such as, for example, "Schedule it for 8:30 on April $3^{rd}$". In response to receiving the second spoken command input, the virtual assistant 102 may transmit the information relating to the user's selection to the second provider server 720 such that the second provider server 720 updates it's scheduling records to include the requested appointment time and date from the user 110. It will be understood that the above scheduling example is for illustrating concepts of the present disclosure and that a number of alternative requests may have been presented such as, for example, but not limited to, if there were no times available within the user's initially requested time frame, if none of the provided times were suitable to the user, if a preferred provider needed to be established.

In some embodiments, the voice-assisted member interface may be configured to generate a visual indication, at virtual assistant 102, in response to a change in the records stored on one or more of the first and second databases 707, 724, that relates to the user 110. The voice-assisted member interface may receive an indication from either the first or second provider server 706, 720, that there is a change in the records stored on the respective databases 707, 724, that relates to the user 110 (e.g., relates to the user's account with the respective provider). A change in the records may be, for example, but not limited to, a quantity of a medicament currently prescribed to the user running low, or put another way, that the user's prescription medication is, or should be based on a prescription regimen, close to being out (e.g., 1-4 days of medication remaining). The change in record may also be more generalized while still pertaining to the user. For example, the change in record may be that season flu shots are now available at a local pharmacy or another location. In response to the change in the records, the voice-assisted member interface may cause the virtual assistant 102 to provide an indication (e.g., a visual indication, a light emission, an audible indication) to the user 110 that the change has occurred and requires the user's attention.

In response to the visual indication, the user 110 may interact with the virtual assistant 102 (e.g., provide a spoken command) to request further information regarding the visual indication (e.g., what the visual indication is specifically related to). The virtual assistant 102, may in response to the interaction from the user 110, and in response to the user 110 having a valid account linking token and/or valid voice biometric data, provide to the user 110 information regarding the visual indication to the user 110. The information may be provided via audio output and/or directing the user 110 to where the further information may be obtained, such as, for example, sending an email that contains said information, or the location where said information may be obtained, to the email address associated with the user's account. In some embodiments, providing Referring to FIGS. 10A-10B, there is shown an exemplary diagram depicting a method of interacting with a voice-assisted member interface hosted by a provider backend server of a provider using a voice enabled-apparatus hosted by an apparatus vendor separate and distinct from the provider. The voice-enabled apparatus may include a microphone unit, a speaker and a processor coupled to the microphone unit and the speaker. The processor may be configured to cause the voice-enabled apparatus to perform one or more functions in response to audio signals received at the microphone unit.

In some embodiments, the method 1000 may include the step 1002 of receiving an audio input signal from a user at the microphone unit of the voice-enabled apparatus. For example, the user 110 may provide a spoken command at virtual assistant 102 that is received by the audio input device 112. In some embodiments, the method 1000 may include the step 1004 of converting, at the voice-enabled apparatus, the audio input signal to a computer readable text format. For example, the virtual assistant 102 may be configured to convert the user's spoken command into a computer readable text format. In some embodiments, the method 1000 may include the step 1006 of transmitting, from the voice-enabled apparatus to the first provider backend server, the converted audio input signal. For example, the virtual assistant 102 may transmit the computer readable text generated by converting the user's spoken command to the first provider server 706. In some embodiments, the method 1000 may include the step 1008 of determining, by the first provider backend server, whether the converted audio input signal includes a request for a service provider search and one or more search criteria. For example, the first provider server 706 may be configured to determine if the computer readable text generated by converting the spoken command from the user 110 includes an invocation, or phrase, which indicates that the user 110 wishes to perform a provider search and whether search criteria was included in the spoken command.

In some embodiments, the method 1000 may include the step 1010 of, in response to the converted audio input signal including a request for a service provider search and one or more search criteria, determining whether a second provider backend server of a second provider includes an associated application programming interface, wherein the second provider is separate and distinct from the first provider. For example, if the spoken command received from user 110 includes a provider search request, the first provider server 706 may be configured to determine whether the second provider server 720 includes a second API 722 associated with the second provider server 720. In some embodiments, the method 1000 may include the step 1012 of, in response to determining that the second provider backend server does include an associated application programming interface, transmitting the one or more search criteria to the associated application programming interface of the second provider backend server. For example, if the second provider server 720 includes an associated second API 722, the first provider server 706 may be configured to transmit the one or more search criteria, included in the computer readable text corresponding to the spoken command, to the second provider server 720.

In some embodiments, the method 1000 may include the step 1014 of executing, by the second provider backend server, a database search in a database in communication with the second provider backend server, based on the one or more search criteria, the database storing a plurality of records corresponding to individual service providers associated with the second provider. For example, the second API 722 may be configured to cause the second provider server 706 to query second database 724 based on the one or more search criteria, such as executing a query to return all healthcare providers who speak a specific language, have a primary specialty as an OB/GYN, and are within a certain radius of the user's home address. In some embodiments, the method 1000 may include the step 1016 of generating, by the second provider backend server, a list of search results including a subset of records, of the plurality of records stored on the database, the subset of records matching the one or more search criteria. For example, based on the query executed on second database 724, the second provider server 720 may generate a list of search results including all healthcare providers which match the search criteria. In some embodiments, the method 1000 may include the step 1018 of transmitting, from the second provider backend server, to the first provider backend server, the list of search results. For example, the second provider server 720 may be configured to transmit the list of search results, including the listing of healthcare providers which match the search criteria, to the first provider server 706.

In some embodiments, the method 1000 may include the step 1020 of generating, from the first provider backend server a response based on the list of search results and transmitting the response to the voice-enabled apparatus. For example, the first provider server 706 may receive the list of search results and generate a response to be returned to the user 110 which includes the listing of healthcare providers matching the search criteria input by the user 110. In some embodiments, the method 1000 may include the step 1022 of outputting, at the speaker, an audio output signal associated with the response. For example, the first provider server 706 may transmit the response to the virtual assistant 102. The virtual assistant 102 may output via an audio output device 114, a display device in communication with the virtual assistant 102, an audio output which includes the listing of the healthcare providers matching the search criteria such that the user 110 can hear and/or see the listing of healthcare providers.

In some embodiments, the method 1000 may further include, in response to determining that the second provider backend server does not include an associated application programming interface, the step of transmitting, from the first provider backend server, to the second provider backend server, a request for the plurality of records corresponding to individual service providers. For example, if no second API 722 is associated with the second provider server 720, the first provider server 706 may transmit a request to the second provider server 720 for healthcare provider records stored on second database 724. In some embodiments, the method 1000 may further include the step of, in response to receiving the request for the plurality of records, transmitting, from the second provider backend server to the first provider backend server, the plurality of records. For example the second provider server 720 may transmit to the first provider server 706 the healthcare provider records stored on second database 724. In some embodiments, the method 1000 may further include the step of executing, by the first provider backend server, a search of the plurality of records, based on the one or more search criteria. For example, in response to receiving the healthcare provider records from the second provider server 720, the first provider server may query the healthcare provider records based on the search criteria.

In some embodiments, the method 1000 may include the step of generating, by the first provider backend server, the list of search results including the subset of records, of the plurality of records received from the second provider backend server, the subset of records matching the one or more search criteria. For example, the first provider server 706 may generate the list of search results based on the query of the received healthcare records. In some embodiments, the method 1000 may further include the steps of generating, from the first provider backend server a response based on the list of search results and transmitting the response to the voice-enabled apparatus, and outputting, at the speaker, an audio output signal associated with the response. For example, the first provider server 706 may generate a response based on the list of search results and transmit the response to the virtual assistant 102 to cause the virtual assistant to output the response to the user 110 as discussed above with reference to steps 1020 and 1022.

In some embodiments, the first provider is a healthcare insurance provider and the second provider is a healthcare provider (e.g., a doctor, hospital, healthcare clinic). In some embodiments, the second provider backend server is a plurality of second provider backend servers each associated with a provider separate and distinct from the first provider. For example, the first provider server 706 may be in communication with a plurality of second provider server 720 and may transmit requests as discussed above to one or more of the plurality of second provider server 720. In some embodiments, the output audio signal includes a prompt to the user to perform a subsequent user action. For example, the audio output signal may include a question to the user 110 such as "would you like anything else?" which prompts the user 110 to provide an invocation which may include a request to perform a subsequent action (e.g., another healthcare provider search). In some embodiments, the voice-enabled apparatus (e.g., virtual assistant 102) is HIPAA compliant.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

What is claimed is:

1. A method for interacting with a voice-assisted member interface hosted by a first provider backend server of a first provider using a voice-enabled apparatus hosted by an apparatus vendor separate and distinct from the first provider, the voice-enabled apparatus including a microphone unit, a speaker and a processor coupled to the microphone unit and the speaker, the processor configured to cause the voice-enabled apparatus to perform one or more functions in response to audio signals received at the microphone unit, the method comprising:

receiving an audio input signal from a user at the microphone unit of the voice-enabled apparatus;

converting, at the voice-enabled apparatus, the audio input signal to a computer readable text format;

transmitting, from the voice-enabled apparatus to the first provider backend server, the converted audio input signal;

determining, by the first provider backend server, whether the converted audio input signal includes a request for a service provider search and one or more search criteria;

in response to the converted audio input signal including a request for a service provider search and one or more search criteria, determining whether a second provider backend server of a second provider includes an associated application programming interface, wherein the second provider is separate and distinct from the first provider;

in response to determining that the second provider backend server does include an associated application programming interface, transmitting the one or more search criteria to the associated application programming interface of the second provider backend server;

executing, by the second provider backend server, a database search in a database in communication with the second provider backend server, based on the one or more search criteria, the database storing a plurality of records corresponding to individual service providers associated with the second provider;

generating, by the second provider backend server, a list of search results including a subset of records, of the plurality of records stored on the database, the subset of records matching the one or more search criteria;

transmitting, from the second provider backend server, to the first provider backend server, the list of search results;

generating, from the first provider backend server, a response based on the list of search results and transmitting the response to the voice-enabled apparatus;

outputting, at the speaker, an audio output signal associated with the response;

in response to determining that the second provider backend server does not include an associated application programming interface;

transmitting, from the first provider backend server, to the second provider backend server, a request for the plurality of records corresponding to individual service providers;

in response to receiving the request for the plurality of records, transmitting, from the second provider backend server to the first provider backend server, the plurality of records;

executing, by the first provider backend server, a search of the plurality of records. based on the one or more search criteria;

generating, by the first provider backend server, the list of search results including the subset of records, of the plurality of records received from the second provider backend server, the subset of records matching the one or more search criteria;

generating, from the first provider backend server, a response based on the list of search results and transmitting the response to the voice-enabled apparatus; and outputting, at the speaker, an audio output signal associated with the response.

2. The method of claim 1, wherein the first provider is a healthcare insurance provider and the second provider is a healthcare provider.

3. The method of claim 1, wherein the second provider backend server is a plurality of second provider backend servers, each associated with a provider separate and distinct from the first provider.

4. The method of claim 1, wherein the output audio signal includes a prompt to the user to perform a subsequent user action.

5. The method of claim 1, wherein the voice-enabled apparatus is HIPAA compliant.

6. The method of claim 1, wherein the one or more search criteria include one or more of gender, age, primary healthcare specialty, and languages spoken.

7. A system for interacting with a voice-assisted member interface hosted by a first provider backend server of a first provider, comprising:

a voice-enabled apparatus including a microphone unit, a speaker and a processor coupled to the microphone unit and the speaker, the processor configured to cause the voice-enabled apparatus to perform one or more functions in response to audio signals received at the microphone unit;

the processor being configured to:
receive an audio input signal from a user at the microphone unit of the voice-enabled apparatus;
convert the audio input signal to a computer readable text format; and
transmit, from the voice-enabled apparatus to the first provider backend server, the converted audio input signal;

a first provider backend server configured to:
determine whether the converted audio input signal includes a request for a service provider search and one or more search criteria;
in response to the converted audio input signal including a request for a service provider search and one or more search criteria, determining whether a second provider backend server of a second provider includes an associated application programming interface, wherein the second provider is separate and distinct from the first provider; and
in response to determining that the second provider backend server does include an associated application programming interface, transmitting the one or more search criteria to the associated application programming interface of the second provider backend server;

a second provider backend server configured to:
execute a database search in a database in communication with the second provider backend server, based on the one or more search criteria, the database storing a plurality of records corresponding to individual service providers associated with the second provider;
generate a list of search results including a subset of records, of the plurality of records stored on the database, the subset of records matching the one or more search criteria; and
transmit, from the second provider backend server, to the first provider backend server, the list of search results;

the first provider backend server further configured to generate a response based on the list of search results and transmitting the response to the voice-enabled apparatus; and the voice-enabled apparatus further configured to output at the speaker, an audio output signal associated with the response;

wherein the first provider backend server is further configured to:
in response to determining that the second provider backend server does not include an associated application programming interface;
transmit to the second provider backend server, a request for the plurality of records corresponding to individual service providers;
wherein the second provider backend server is further configured to:
in response to receiving the request for the plurality of records, transmitting, from the second provider backend server to the first provider backend server, the plurality of records;
wherein the first provider backend server is further configured to:
execute a search of the plurality of records, based on the one or more search criteria;
generate the list of search results including the subset of records, of the plurality of records received from the second provider backend server, the subset of records matching the one or more search criteria; and
generate a response based on the list of search results and transmit the response to the voice-enabled apparatus.

8. The system of claim 7, wherein the first provider is a healthcare insurance provider and the second provider is a healthcare provider.

9. The system of claim 7, wherein the second provider backend server is a plurality of second provider backend servers, each associated with a provider separate and distinct from the first provider.

10. The system of claim 7, wherein the output audio signal includes a prompt to the user to perform a subsequent user action.

11. The system of claim 7, wherein the processor is further configured to:
before linking a first user account to a second user account, determine that a voice biometric data profile associated with the user is stored on the vendor backend server;
in response to the voice biometric data profile not being stored on the vendor backend server, conduct voice biometric training using audio signals from the user to generate the voice biometric data profile; and
the vendor backend server further configured to:
associate the generated voice biometric data profile with the first user account and storing the generated voice biometric data profile; and
in response to the voice biometric data profile being stored on the vendor backend server, link the first user account to the second user account.

12. The system of claim 7, wherein the voice-enabled apparatus is HIPAA compliant.

13. A method for interacting with a voice-assisted member interface hosted by a provider backend server of a provider using a voice enabled-apparatus hosted by an apparatus vendor separate and distinct from the provider, the voice-enabled apparatus including a microphone unit, a speaker and a processor coupled to the microphone unit and the speaker, the processor configured to cause the voice-enabled apparatus to perform one or more functions in response to audio signals received at the microphone unit, the method comprising:
receiving, at a user interface associated with the voice-enabled apparatus, first authentication credentials associated with the vendor of the voice-enabled apparatus;
transmitting, by the processor of the voice-enabled apparatus to a vendor backend server of the voice-enabled apparatus, a first request to authenticate a user at the voice-enabled apparatus, the first request including the first authentication credentials and a unique identifier of the voice-enabled apparatus;
authenticating, at the vendor backend server, the first user account using the first authentication credentials and the unique identifier of the voice-enabled apparatus and linking the first user account to the voice-enabled apparatus;
receiving, at a user interface associated with the voice-enabled apparatus and operated by the user, a second request to link the first user account with a second user account, the second request including second authentication credentials associated with a second user account at the provider;
transmitting, by the user interface to a provider backend server of the provider, a request to authenticate the second user account at the voice-enabled apparatus, the request including the second authentication credentials;
authenticating, at the provider backend server of the provider, the second user account and linking the first user account to the second user account at the voice-enabled apparatus;
receiving an input audio signal from the user at the microphone unit of the voice-enabled apparatus;
determining, by the processor, that the second audio signal includes vocal attribute data associated with the user;
determining, by the processor, that the second audio signal includes a portion of speech associated with a command to execute a requested functionality of the voice-assisted member interface;
validating, that the vocal attribute data matches a voice biometric profile associated with the user;
transmitting, by the processor to the provider backend server, the command to execute the requested functionality of the voice-assisted member interface;
validating, at the provider backend server, that the command from the voice-enabled apparatus is associated with an active account at the provider;
in response to the vocal attribute data matching the voice biometric profile and the command from the voice-enabled apparatus being associated with an active account at the provider, executing, by the provider backend server, the requested functionality of the voice-assisted member interface;
generating, by the provider backend server, a response for the user and transmitting the response to the voice-enabled apparatus;
outputting, at the speaker, an output audio signal associated with the response;
receiving an audio input signal from a user at the microphone unit of the voice-enabled apparatus;
converting, at the voice-enabled apparatus, the audio input signal to a computer readable text format;
transmitting, from the voice-enabled apparatus to the vendor server, the converted audio input signal;
determining, by the vendor server, whether the converted audio input signal includes a request for a service provider search and one or more search criteria;
in response to the converted audio input signal including a request for a service provider search and one or more search criteria, determining whether a provider backend server of a provider includes an associated application programming interface, wherein the provider is separate and distinct from the vendor;

in response to determining that the provider backend server does include an associated application programming interface, transmitting the one or more search criteria to the associated application programming interface of the provider backend server;

executing, by the provider backend server, a database search in a database in communication with the provider backend server, based on the one or more search criteria, the database storing a plurality of records corresponding to individual service providers associated with the second provider;

generating, by the provider backend server, a list of search results including a subset of records, of the plurality of records stored on the database, the subset of records matching the one or more search criteria;

transmitting, from the provider backend server, to the vendor server, the list of search results;

generating, from the vendor server a response based on the list of search results and transmitting the response to the voice-enabled apparatus;

outputting, at the speaker, an audio output signal associated with the response;

in response to determining that the provider backend server does not include an associated application programming interface;

transmitting, from the vendor server, to the provider backend server, a request for the plurality of records corresponding to individual service providers;

in response to receiving the request for the plurality of records, transmitting, from the provider backend server to the vendor server, the plurality of records;

executing, by the vendor server, a search of the plurality of records, based on the one or more search criteria;

generating, by the vendor server, the list of search results including the subset of records, of the plurality of records received from the provider backend server, the subset of records matching the one or more search criteria;

generating, from the vendor server a response based on the list of search results and transmitting the response to the voice-enabled apparatus; and outputting, at the speaker, an audio output signal associated with the response.

\* \* \* \* \*